(12) United States Patent
Akhoury et al.

(10) Patent No.: US 8,436,116 B2
(45) Date of Patent: May 7, 2013

(54) RESPONSIVE MATERIALS FOR ISOLATING ORGANIC COMPOUNDS

(75) Inventors: Abhinav Akhoury, Cambridge, MA (US); Lev E. Bromberg, Swampscott, MA (US); Trevor Alan Hatton, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 640 days.

(21) Appl. No.: 12/395,004

(22) Filed: Feb. 27, 2009

(65) Prior Publication Data

US 2010/0222519 A1    Sep. 2, 2010

(51) Int. Cl.
*C08F 30/04* (2006.01)
*C08F 20/44* (2006.01)
*C08F 118/02* (2006.01)

(52) U.S. Cl.
USPC .................. 526/240; 526/317.1; 526/319

(58) Field of Classification Search .................. 526/240, 526/317.1, 319
See application file for complete search history.

(56) References Cited

U.S. PATENT DOCUMENTS

| | | | | |
|---|---|---|---|---|
| 3,813,307 | A * | 5/1974 | Burnett ...................... | 149/19.91 |
| 3,886,192 | A * | 5/1975 | Reed, Jr. ........................ | 556/144 |
| 4,001,194 | A * | 1/1977 | Floyd ............................ | 526/240 |
| 4,910,234 | A * | 3/1990 | Yamamori et al. ......... | 424/78.09 |
| 5,442,023 | A * | 8/1995 | Argyropoulos et al. ...... | 526/320 |
| 2006/0025550 | A1* | 2/2006 | Liu et al. ........................ | 526/319 |

OTHER PUBLICATIONS

Amiya, T. et al., "Phase Transitions in Cross-Linked Gels of Natural Polymers", *Macromolecules*, 20:1162-1164 (American Chemical Society, 1987).
Bonnefoi, L. et al., "Electrode compositions for carbon power supercapacitors", *Journal of Power Sources*, 80:149-155 (Elsevier Science S.A., 1999).
Bu, H-z. et al., "Characterization of a Ferrocene-Containing Polyacrylamide-Based Redox Gel for Biosensor Use", *Anal. Chem.*, 67:4071-4076 (American Chemical Society, Nov. 15, 1995).
Datwani, S. S. et al., "Redox-Dependent Surface Tension and Surface Phase Transitions of a Ferrocenyl Surfactant: Equilibrium and Dynamic Analyses with Fluorescence Images", *Langmuir*, 19:8292-8301 (American Chemical Society, 2003).
Fransson, L. et al., "Influence of carbon black and binder on Li-ion batteries", *Journal of Power Sources*, 101:1-9 (Elsevier Science B.V., 2001).
Fujiki, K. et al., "Radical Grafting from Carbon Black. Graft Polymerization of Vinyl Monomers Initiated by Azo Groups Introduced onto Carbon Black Surface", *Polymer Journal*, 22(8):661-670 (Nigata, Japan 1990).
Fujiki, K. et al., "Radical grafting from carbon fiber surface: graft polymerization of vinyl monomers initiated by azo groups introduced onto the surface", *Composite Interfaces*, 3(5/6):371-380 (Nigata, Japan 1996).

(Continued)

*Primary Examiner* — William Cheung
(74) *Attorney, Agent, or Firm* — Alan W. Steele; Foley Hoag LLP

(57) ABSTRACT

One aspect of the present invention relates to polymers containing redox-responsive moieties (such as, ferrocene). In certain embodiments, the present invention relates to in-situ continuous separation systems which use such redox-responsive polymers for low-molecular weight alcohol removal from an aqueous mixture; such systems enhance the production of low-molecular weight alcohols by reducing the product inhibition effects that plague their production from biomass by fermentation.

11 Claims, 11 Drawing Sheets

| Name of gel | mole % of constituents | | | | |
|---|---|---|---|---|---|
| | HBMA | VF | BIS | EGDMA | AIBN |
| HBMA | 95.60 | - | 2.27 | - | 2.13 |
| HBMA-VF-1 | 95.42 | 1.40 | 1.64 | - | 1.54 |
| HBMA-VF-2 | 93.94 | 2.35 | 1.88 | - | 1.83 |
| HBMA-VF-3 | 66.97 | 19.85 | - | 8.37 | 4.81 |
| HBMA-VF-4 | 72.91 | 21.61 | - | 3.04 | 2.44 |
| HBMA-VF-5 | 72.91 | 21.61 | - | 3.04 | 2.44* |

* added sequentially at 30 minute intervals in three equal parts

OTHER PUBLICATIONS

Gallardo, B. S. et al., "Ferrocenyl Surfactants at the Surface of Water: Principles for Active Control of Interfacial Properties", *Langmuir*, 12:4116-4124 (American Chemical Society, 1996).

Groot, W. J. et al., "Butanol recovery from fermentations by liquid-liquid extraction and membrane solvent extraction", *Bioprocess Engineering*, 5:203-216 (Springer-Verlag 1990).

Groot, W. J. et al., "Technologies for Butanol Recovery Integrated with Fermentations", *Process Biochemistry*, 27:61-75 (Elsevier Science Publishers Ltd., England, 1992).

Hirokawa, Y, et al., "Volume phase transition in a nonionic gel", *J. Chem. Phys.*, 81(12), Pt. II, 6379-6380 (American Insitute of Physics, 1984).

Hoshino, K. et al., "Electrochemical Formation of an Organic Thin Film by Disruption of Micelles", *J. Am. Chem. Soc.*, 109:5881-5883 (American Chemical Society, 1987).

Ilmain, F. et al., "Volume transition in a gel driven by hydrogen bonding", *Nature*, 349:400-401 (Nature Publishing Group, USA, Jan. 31, 1991).

Inomata, H. et al., "Phase Transition of N-Substituted Acrylamide Gels", *Macromolecules*, 23:4887-4888 (American Chemical Society, 1990).

Kealy, T. J. et al., "A New Type of Organo-Iron Compound", *Nature*, 168(4286):1039-1040 (Nature Publishing Group, 1951).

Koullas, D. P. et al., "Solvent Selection for the Extraction of Ethanol from Aqueous Solutions", *Separation Science and Technology*, 34(11):2153-2163 (Marcel Dekker, Inc. 1999).

Munson, C. L. et al., "Factors Influencing Solvent Selection for Extraction of Ethanol from Aqueous Solutions", *Ind. Eng. Chem. Process Des. Dev.*, 23:109-115 (American Chemical Society, 1983).

Nakahama, S. et al., "The Effect of Composition of a Ferrocene-Containing Redox Polymer on the Electrochemistry of its Thin Film Coatings on Electrodes", *J. Electroanal. Chem.*, 158:303-322 (Elsevier Sequoia S.A., 1983).

Nesmeyanov, A. N. et al., "Principal Practical Applications of Ferrocene and Its Derivatives", *Russian Chemical Reviews* (translation), 43(9):710-715 (USSR Academy of Sciences, Moscow, 1974).

Offeman, R. D. et al., "Solvent Extraction of Ethanol from Aqueous Solutions. I. Screening Methodology for Solvents", *Ind. Eng. Chem. Res.*, 44:6789-6796 (American Chemical Society, 2005).

Offeman, R. D. et al., "Solvent Extraction of Ethanol from Aqueous Solutions. II. Linear, Branched, and Ring-Containing Alcohol Solvents", *Ind. Eng. Chem. Res.*, 44:6797-6803 (American Chemical Society, 2005).

Onuki, A., "Volume-Phase Transition in Constrained Gels", *Journal of the Physical Society of Japan*, 57(6):1868-1871 (Kyoto, Japan, Jun. 6, 1988).

Onuki, A., "Pattern Formation in Gels", *Journal of the Physical Society of Japan*, 57(3):703-706 (Kyoto, Japan, Mar. 3, 1988).

Roddy, J. W., "Distribution of Ethanol-Water Mixtures to Organic Liquids", *Ind. Eng. Chem. Process Des. Dev.*, 20-104-108 (American Chemical Society, 1981).

Roffler, S. R. et al., "In-situ recovery of butanol during fermentation", *Bioprocess Engineering*, 2:1-12 (Springer-Verlag 1987).

Saji, T. et al., "Reversible Formation and Disruption of Micelles by Control of the Redox State of the Surfactant Tail Group", *J. Chem. Soc., Chem. Commun.*, 865-866 (Tokyo, Japan, 1985).

Saji, T. et al., "Reversible Formation and Disruption of Micelles by Control of Redox State of the Head Group", *J. Am. Chem. Soc.*, 107:6865-6868 (American Chemical Society, 1985).

Sasaki, Y. et al., "Organometallic Polymers. XXV. Preparation of Polyvinylferrocene", *Journal of Polymer Science*, 11:1213-1224 (John Wiley & Sons, Inc., USA, 1973).

Tamaki, T. et al., "High-Surface-Area Three-Dimensional Biofuel Cell Electrode Using Redox-Polymer-Grafted Carbon", *Ind. Eng. Chem. Res.*, 45:3050-3058 (American Chemical Society, 2006).

Tanaka, T., "Collapse of Gels and the Critical Endpoint", *Physical Review Letters*, 40(12):820-823 (The American Physical Society, 1978).

Tanaka, T. et al., "Phase Transitions in Ionic Gels", *Physical Review Letters*, 45(20):1636-1639 (American Physical Society, Nov. 17, 1980).

Tatsuma, T. et al., "A Redox Gel. Electrochemically Controllable Phase Transition and Thermally Controllable Electrochemistry", *Macromolecules*, 27:6687-6689 (American Chemical Society, 1994).

Tsiafoulis, C. G. et al., "Electrochemical study of ferrocene intercalated vanadium pentoxide xerogel/polyvinyl alcohol composite films: Application in the development of amperometric biosensors", *Electrochemistry Communications*, 7:781-788 (Elsevier B.V., 2005).

\* cited by examiner

| Name of gel | mole % of constituents | | | | |
|---|---|---|---|---|---|
| | HBMA | VF | BIS | EGDMA | AIBN |
| HBMA | 95.60 | - | 2.27 | - | 2.13 |
| HBMA-VF-1 | 95.42 | 1.40 | 1.64 | - | 1.54 |
| HBMA-VF-2 | 93.94 | 2.35 | 1.88 | - | 1.83 |
| HBMA-VF-3 | 66.97 | 19.85 | - | 8.37 | 4.81 |
| HBMA-VF-4 | 72.91 | 21.61 | - | 3.04 | 2.44 |
| HBMA-VF-5 | 72.91 | 21.61 | - | 3.04 | 2.44* |

* added sequentially at 30 minute intervals in three equal parts

*Reduced State*

*Oxidized State*

Heated at 80° C to form a gel

RESPONSIVE MATERIALS FOR ISOLATING ORGANIC COMPOUNDS

BACKGROUND

Liquid-liquid extraction, commonly known as solvent extraction, is a technique for separating the components of a solution by distribution between two liquid phases [T C Lo; M H I Baird; C Hanson (Ed), *Handbook of Solvent Extraction*, John Wiley & Sons, New York, 1983]. With increasing understanding of solvent extraction, it was first shown as a possible technique to separate alcohols from water in the 1940s [D F Othmer; E Trueger, *Transact. AIChE*, 1941, 37, 597]. The energy crisis in the 1970s forced the scientific community to look for alternatives to conventional petroleum-based fuels and to use alcohols as additives to gasoline. It is only since then that significant attention has been paid to the use of solvent extraction as a possible alternative to distillation for alcohol separation and concentration [J W Roddy, *Ind. Eng. Chem. Process Des. Dev.*, 1981, 20, 104-108].

The choice of a solvent to be used to achieve effective separation of the constituents of a given solution is guided by an estimation of two parameters, namely the equilibrium distribution coefficient ($K_D$) and the separation factor ($\alpha$). In the context of extraction of alcohol from an aqueous solution, the equilibrium distribution coefficient may be defined as the ratio of the weight fraction of alcohol in the added solvent to that in the aqueous phase. A high value of $K_D$ requires only a low solvent-to-water ratio for effective extraction. The separation factor, defined as the ratio of the equilibrium distribution coefficient of alcohol to that of water, gives a measure of the selectivity of the added solvent in extracting alcohol preferentially over water [C L Munson; C Judson King, *Ind. Eng. Chem. Process Des. Dev.*, 1984, 23, 109-115]. The solvent should also have a high capacity for the alcohol as well as low solubility in water. The density difference between solvent and aqueous phases should be such that rapid phase separation takes place [R D Offeman; S K Stephenson; G H Robertson; W J Orts, *Ind. Eng. Chem. Res.*, 2005, 44, 6789-6796]. Along with the estimation of these parameters, two additional considerations need to be kept in mind while evaluating the performance of a solvent. Since alcohol has to be removed from the fermentation broth, care needs to be taken to ensure bio-compatibility of the solvent so that it does not result in the death of the cells carrying out fermentation. Moreover, obtaining a solvent phase rich in alcohol is only one half of the process. Release of alcohol from the solvent into a desired medium and subsequent solvent regeneration form the other half to complete the process. Therefore, the solvent chosen should be such that both of the above mentioned steps can be carried out with technical ease and in an economically viable way.

The ability of different organic solvents to extract ethanol from its dilute solution has been studied extensively in literature. Roddy [J W Roddy, *Ind. Eng. Chem. Process Des. Dev.*, 1981, 20, 104-108] was the first to identify the need for comparative study of performance of different solvents and carried out experiments to evaluate $K_D$ and $\alpha$ for a variety of solvents. It was found that the ethanol extracting potential of the solvent increased in the following order: hydrocarbon=halocarbon<ether<ketone<amine<ester<alcohol.

It was suggested that for a solvent to be effective, keeping process design considerations in mind, we need $K_{D,ethanol}$>0.5 and $\alpha$>10. Munson and King [C L Munson; C Judson King, *Ind. Eng. Chem. Process Des. Dev.*, 1984, 23, 109-115] also carried out a study similar to that of Roddy and highlighted the trade off between equilibrium distribution for ethanol and selectivity. They also found that solvents which behaved as Lewis acids had a more favorable combination Of $K_{D,ethanol}$ and $\alpha$ than did other solvents. They reported that solvent mixtures could have values of $K_{D,ethanol}$ and $\alpha$ which were vastly different from what would be obtained by linear interpolation of the values for the solvent constituents. The values obtained by Munson and King supported Roddy's [J W Roddy, *Ind. Eng. Chem. Process Des. Dev.*, 1981, 20, 104-108] findings of alcohols, acids and ketones being good solvents for ethanol extraction. In particular, MIBK as well as a 62.8% w/w mixture of 2-ethylhexanoic acid with MIBK were found to be effective in extracting ethanol. Alcohols and esters have also been found to be effective solvents for ethanol extraction by Koullas et al. [D P Koullas; O S Umealu; E G Koukios, *Sep. Sci. Technol.*, 1999, 34, 2153-2163].

Recently, Offeman and co-workers [R D Offeman; S K Stephenson; G H Robertson; W J Orts, *Ind. Eng. Chem. Res.*, 2005, 44, 6789-6796; and R D Offeman; S K Stephenson; G H Robertson; W J Orts, *Ind. Eng. Chem. Res.*, 2005, 44, 6797-6803] focused their attention on the ethanol extraction potential of alcohols and studied the effect of the alcohol molecular weight and structure on this potential. $K_{D,ethanol}$ and $K_{D,water}$ have been found to be dependent on the point of branching of the carbon chain in the alcohol, length of the branches and the main chain and location of the hydroxyl group along the chain length. Alcohols containing rings were found to have values of a less than the aliphatic alcohols. The trade off between $K_{D,ethanol}$ and $\alpha$ was reconfirmed.

Butanol, like ethanol, is produced by fermentation of sugars or starches. Several technologies, apart from distillation, have been tested for separating the butanol produced from fermentation broths. Liquid-liquid extraction has been shown by Groot et al. [W J Groot; H S Soedjak; P B Donck; R G J M van der Lans; K C A M Luyben; J M K Timmer, *Bioprocess. Eng.*, 1990, 5, 203-216; and W J Groot; R G J M van der Lans; K C A M Luyben, *Process Biochem.*, 1992, 27, 61-75] to be one of the techniques with the greatest potential because the solvents can be selected to give a high selectivity for butanol over water and also because of the possibility to carry out the extraction in-situ. Solvents like kerosene, dodecanol, tetradecanol, oleyl alcohol and benzyl benzoate have been tested for the ability to extract ethanol by Roffler and co-workers [S R Roffler; H W Blanch; C R Wilke, *Bioprocess. Eng.*, 1987, 2, 1-12]. Oleyl alcohol and 50 wt % of oleyl alcohol in benzyl benzoate have been shown to be most effective among the solvents tested, for the extraction of butanol.

Solubility parameters are used to assign a numerical value to the solvency behavior of a specific solvent. They have been widely used to aid in solvent selection. A single value of a solubility parameter for each solvent, as proposed by Hildebrand, did not completely capture the several interactions that take place between the solvent and solute molecules and lead to the solvation. To overcome this drawback, Hansen proposed the use of a set of three solubility parameters to describe a solvent's ability to dissolve a solute. The three parameters accounted for the dispersion characteristics ($\delta_D$), the polar characteristics ($\delta_P$), and the hydrogen bonding ability ($\delta_H$) of the solvent molecule. Hansen plotted the location of different solvents in a three dimensional space formed by the three solubility parameters. It is found that in this three dimensional "solubility space", there exists a region around each solvent, molecules lying in which can be dissolved by the solvent. If the dispersion parameter is doubled, this region assumes a spherical shape centered on the location of the solvent of interest. The radius of this solubility sphere, called the interaction radius (Ro), is characteristic of each solvent molecule and can be determined experimentally. Distance between two molecules in this modified "solubility space", Ra, can be calculated according to the following formula:

$$(Ra)^2 = 4(\delta_{D2}-\delta_{D1})^2 + (\delta_{P2}-\delta_{P1})^2 + (\delta_{H2}-\delta_{H1})^2 \qquad (1)$$

Hence, the condition for solubility of one substance in another can be mathematically expressed as:

$$Ra/Ro \leq 1 \qquad (2)$$

The three solubility parameters for a wide range of solvents and polymers as well as their interaction radius are reported in the literature [C M Hansen, *Hansen Solubility Parameters: A User's Handbook*, 2nd, CRC Press; 2007]. A rough estimate of Ro for a substance can be made by calculating the distance of its molecule from various solvents, which have been shown in literature to dissolve the substance of interest in the "solubility space", and choosing the largest among the calculated values.

The change in the volume of a gel in response to change(s) in its environment is known as the volume phase transition of the gel. Since the discovery of this interesting phenomenon in 1978 [T Tanaka, *Phys. Rev. Lett.*, 1978, 40, 820-823], it has been the subject of extensive research. For example, Shibayama and Tanaka in their review of gel properties [M Shibayama; T Tanaka, "Volume Phase Transition and Related Phenomena of Polymer Gels", In *Responsive Gels: Volume Transitions I*. Edited by K Dusek: Springer; 1993, 1-62. Advances in Polymer Science, vol 109] describe the thermodynamic behavior of polymer gels using the Flory-Rehner model [P J Flory, *Principles of Polymer Chemistry*. Ithaca, Cornell University Press; 1953] which describes the free energy change involved in the mixing of solvent with a polymeric gel network as a function of the volume fraction of the polymer, volume of each lattice site, temperature and Flory's interaction parameter, $\chi$. The phase diagram thus obtained predicts discontinuous volume phase transitions in polymer solutions at different temperatures. More advanced theories predicting similar volume phase transition in gels and their equation of state can be found in the work by Khokhlov and Nechaev [A R Khokhlov; K A Khachaturian, *Polymer*, 1982, 23, 1742-1750]. Amiya and Tanaka have shown that discontinuous volume phase transition is not restricted only to synthetic gels (like acrylamide gels) but is a universal property of all gels [T Amiya; T Tanaka, *Macromolecules*, 1987, 20, 1162-1164].

Volume phase transition of gels is a consequence of changes in either intra-molecular interactions or the interactions between the polymer gel and the solvent medium. These interactions fall in one of the following categories: van der Waals interactions, hydrophobic interactions, hydrogen bonding and electrostatic interactions [F Ilmain; T Tanaka; E Kokufuta, *Nature*, 1991, 349, 400-401]. The swelling behavior of acrylamide gels in response to changes in the concentration of solvent or system temperature has been attributed to the van der Waals effect [T Tanaka; D Fillmore; S-T Sun; I Nishio; G Swislow; A Shah, *Phys. Rev. Lett.*, 1980, 45, 1636-1639]. The swelling behavior of natural polymers like DNA when the solvent quality is changed has also been shown to be a result of van der Waals interaction [T Amiya; T Tanaka, *Macromolecules*, 1987, 20, 1162-1164]. The increase in entropy of the system due to break-down of the ordered structure of water molecules in the vicinity of hydrophobic segments of polymer gels in response to increase in temperature, leads to swelling of the non ionic gels like N-isopropylacrylamide gels [Y Hirokawa; T Tanaka, *J. Chem. Phys.*, 1984, 81, 6379-6380]. Also, it has been found that the temperature at which volume phase transition due to hydrophobic interaction takes place is dependent on the surface area of the hydrophobic segments of the gel [H Inomata; S Goto; S Saito, *Macromolecules*, 1990, 23, 4887-4888]. Ilmain and co workers [F Ilmain; T Tanaka; E Kokufuta, *Nature*, 1991, 349, 400-401] have proven that the swelling and collapse of the interpenetrating polymer network formed by poly(acrylamide) and poly(acrylic acid) when the temperature is cyclically varied is due to the hydrogen bonding between the acid and amide groups in the molecule. Addition of urea, which is known to disrupt hydrogen bonding, caused the volume phase transition to disappear and the gels were found to be swollen at all temperatures. If the polymer chain has charged groups attached to the backbone, ionic interactions come into play. Since ionization of the groups depends on the pH of the medium, gels can be swollen or contracted by repulsive and attractive electrostatic interactions respectively as the pH of the medium is varied [A Myoga; S Katayama, *Polym. Prep. Japan*, 1987, 36, 2852-2854].

As discussed above, the change in interactions within a gel system can be triggered by changing any of a number of different stimuli. The most commonly used stimulus is temperature [F Ilmain; T Tanaka; E Kokufuta, *Nature*, 1991, 349, 400-401; and T Tanaka; D Fillmore; S-T Sun; I Nishio; G Swislow; A Shah, *Phys. Rev. Lett.*, 1980, 45, 1636-1639]. A change in the solvent quality can also cause the gel swelling or contraction [T Amiya; T Tanaka, *Macromolecules*, 1987, 20, 1162-1164]. Gels which have charged groups respond to changes in pH of the solvent medium [A Myoga; S Katayama, *Polym. Prep. Japan*, 1987, 36, 2852-2854]. Gels may be designed to respond to light. Light can either cause ionization of groups within the polymer, thus leading to charge interactions [A Mamada; T Tanaka; D Kungwatchakun; M Irie, *Macromolecules*, 1990, 23, 1517-1519], or can cause local heating of polymer segments [A Suzuki; T Tanaka, *Nature*, 1990, 346, 345-347]. Gels may also be designed to respond to presence of some particular molecules [E Kokufuta; T Tanaka, *Macromolecules*, 1991, 24, 1605-1607] and stress [A Onuki, *J. Phys. Soc. Jpn.*, 1988, 57, 1868-1871; and A Onuki, *J. Phys. Soc. Jpn.*, 1988, 57, 703-706] but examples of systems which respond to these stimuli are fewer in literature.

The discovery of ferrocene in early 1950s [T J Kealy; P L Pauson, *Nature*, 1951, 168, 1039-1040] drew the attention of the scientific community to this metallocene, as it possessed a vast organic chemistry, enabling easy attachment of the ferrocene group to other organic compounds, and also underwent reversible one electron oxidation to ferrocenium ion [I Manners, "Side-Chain Metal-Containing Polymers", In *Synthetic Metal-Containing Polymers*. Edited by I Manners: Wiley-VCH Verlag GmbH & Co. KGaA; 2004, 39]. For the first couple of decades after the discovery, the chemists around the world made efforts to understand the chemistry of ferrocene. This was followed by reports of several possible practical applications of ferrocene and its derivatives. The applications can be broadly grouped in the following classes: components of redox systems, effective nontoxic medicinal substances, absorbers of different types of radiation, and others [A N Nesmeyanov; N S Kochetkova, *Russ. Chem. Rev.*, 1974, 43, 710-715].

Saji and coworkers pioneered the control of a molecule's properties by manipulating the oxidation state of the ferrocenyl group attached to the molecule. The ferrocenyl group attached to the head [T Saji; K Hoshino; S Aoyagui, *J. Amer. Chem. Soc.*, 1985, 107, 6865-6868] or the tail [T Saji; K Hoshino; S Aoyagui, *J. Chem. Soc., Chem. Commun.*, 1985, 865-866] of surfactant molecules was reversibly oxidized and reduced, and the corresponding change in the dynamic properties, like the self-assembling behavior, of the micelles was observed. It was found that the introduction of charge in the surfactant molecules by oxidation of the ferrocenyl group led to disruption of the surfactant's micellar structure. This was attributed to an increase in the hydrophilicity of the molecule. The phenomenon of disruption of micellar structure has been used for formation of organic thin films [T Saji; K Hoshino; Y Ishii; M Goto, *J. Amer. Chem. Soc.,* 1991, 113, 450-456; and K Hoshino; T Saji, *J. Amer. Chem. Soc.,* 1987, 109, 5881-1883]. Abbott and his group used the technique developed by Saji and coworkers [T Saji; K Hoshino; Y Ishii; M Goto, *J. Amer. Chem. Soc.,* 1991, 113, 450-456] for the synthesis of surfactant molecules with attached ferrocenyl group and studied the change in surface tension of the aqueous solution of the surfactant on oxidation of the ferrocenyl group [S S Datwani; V N Truskett; C A Rosslee; N L Abbott; K J Stebe, *Langmuir,* 2003, 19, 8292-8301; B S Gallardo; M J Hwa; N L Abbott, *Langmuir,* 1995, 11, 4209-4212; and B S Gallardo; K L Metcalfe; N L Abbott, *Langmuir,* 1996, 12, 4116-4124].

Applications of polymer gels containing ferrocenyl groups have been reported in the literature. Such gels, referred to as redox gels, have been widely shown to work as electrochemical biosensors. Bu et al. synthesized polyacrylamide gel with attached ferrocenyl group and containing entrapped glucose oxidase [H-z Bu; S R Mikkelsen; A M English, *Anal. Chem.,* 1995, 67, 4071-4076]. The gel was attached to a carbon paste electrode. Current flowing during cyclic voltammetry of the electrode dipped in an electrolyte solution was shown to be sensitive to the presence of glucose in the solution. Recently Tsiafoulis et al. have developed a glucose biosensor based on ferrocene intercalated vanadium pentoxide xerogel/polyvinyl alcohol composite film [C G Tsiafoulis; A B Florou; P N Trikalitis; T Bakas; M I Prodromidis, *Electrochem. Commun.,* 2005, 7, 781-788].

Tatsuma et al. synthesized a temperature responsive redox gel of N-isopropyl-acrylamide (NIPA), vinylferrocene (VF) and N,N'-methylenebisacrylamide (BIS) [T Tatsuma; T Kazutake; H Matsui; N Oyama, *Macromolecules,* 1994, 27, 6687-6689]. It was shown that the increase in hydrophilicity of the redox gel on oxidation of the ferrocenyl groups caused an increase in the phase transition temperature of the gel. The results of this work demonstrate that properties of gels containing ferrocenyl groups are sensitive to the oxidation state of the group and that hydrophilicity of the gels increases when the ferrocenyl groups are charged.

SUMMARY

One aspect of the present invention relates to polymers containing redox-responsive moieties (such as ferrocene) wherein the hydrophilicity of the polymer increases upon oxidation of the redox-responsive moieties. In certain embodiments, the present invention relates to in-situ continuous separation systems which use such redox-responsive polymers for low-molecular weight alcohol removal (by using the polymers to bind alcohol in their reduced state and release the bound alcohol when the polymer is oxidized); such systems may enhance the production of low-molecular weight alcohols by reducing the product inhibition effects that plague their production from bio-mass by fermentation process.

DETAILED DESCRIPTION

Figures 1, 2:
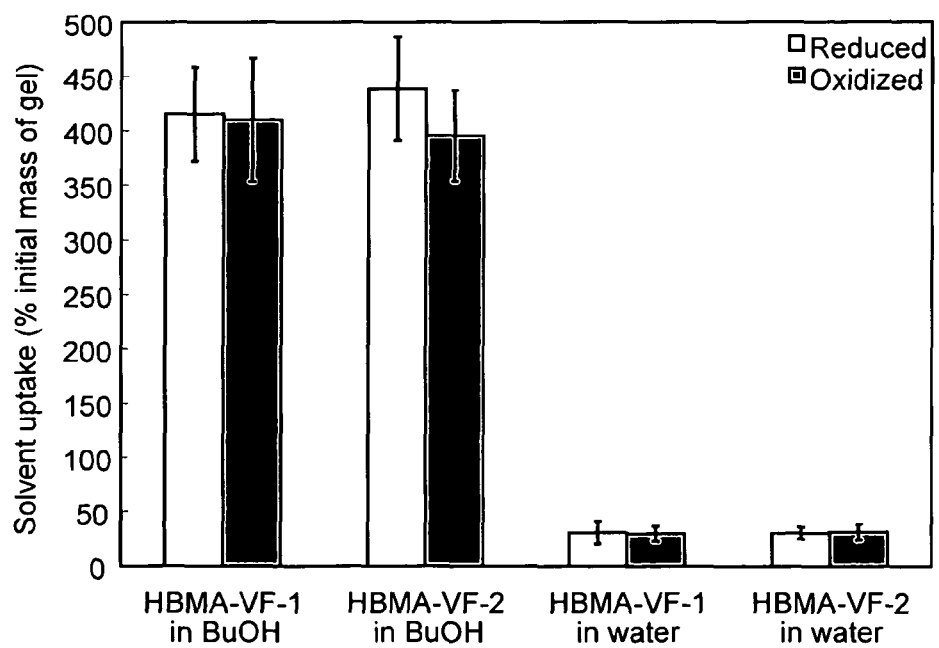
FIG. 1 depicts a table with the molar compositions of HBMA-VF-1 to HBMA-VF-5, which are made from hydroxybutyl methacrylate (HBMA) and vinylferrocene (VF) co-monomers, cross-linked using N,N'-methylenebisacrylamide (BIS) or ethylene glycol dimethacrylate (EGDMA), and initiated using 2,2'-azobis(isobutyronitrile) (AIBN).
FIG. 2 depicts a bar graph showing the uptake of solvent by HBMA-VF-1 and HBMA-VF-2 gels (having low VF content) in reduced and oxidized states. Although HBMA-VF-1 and HBMA-VF-2 uptake a lot of butanol and very little water, their preference for both these compounds is not much different in the oxidized state.

Stimuli-responsive polymers are "smart" materials that change their properties in response to the application of an appropriate stimulus. One aspect of the present invention relates to stimuli-responsive polymers which contain redox-responsive moieties and methods of their use. For example, it is disclosed herein that polymers containing redox-responsive moieties in the uncharged state may be used to selectively extract alcohols of interest from a fermentation broth. After extraction, the application of electric potential to the polymer containing redox-responsive moieties can change the oxidation state of the redox-responsive moieties, increasing the hydrophilicity of the polymer, and thereby result in a release of bound alcohol into a desired medium, as a result of the alcohol being displaced by water. It follows that such polymers could be used in in-situ continuous separation systems to remove low-molecular weight alcohol from aqueous fermentation mixtures. It follows that use of polymers containing redox-responsive moieties can thereby enhance the production of low-molecular weight alcohols by reducing the product inhibition effects that plague their production from bio-mass by fermentation process.

Selected Polymers

One aspect of the invention relates to a polymer comprising a plurality of first subunits, wherein each of the first subunits comprises a redox-responsive moiety. In certain embodiments, the present invention relates to any of the aforementioned polymers, wherein the polymer preferentially binds to an alcohol over water when the redox-responsive moieties are uncharged; and the polymer preferentially binds to water over the alcohol when the redox-responsive moieties are charged.

In certain embodiments, the present invention relates to any of the aforementioned polymers, wherein the alcohol is a $C_2$-$C_5$ alcohol. In certain embodiments, the present invention relates to any of the aforementioned polymers, wherein the alcohol is butanol.

In certain embodiments, the present invention relates to any of the aforementioned polymers, further comprising a plurality of second subunits, wherein each of the second subunits comprises a hydrophobic group.

In certain embodiments, the present invention relates to any of the aforementioned polymers, further comprising a plurality of crosslinked subunits.

In certain embodiments, the present invention relates to any of the aforementioned polymers, wherein the redox-responsive moieties are part of the backbone of the polymer or part of the side chains of the polymer.

In certain embodiments, the present invention relates to any of the aforementioned polymers, wherein the redox-responsive moieties are metallocenes. In certain embodiments, the present invention relates to any of the aforementioned polymers, wherein the redox-responsive moieties are ferrocenes, nickelocenes, cobaltocenes, zirconocenes, ruthenocenes, chromocenes, hafnocenenes, titanocenes, molybdenocenes, niobocenes, tungstenocenes, or vanadocenes. In certain embodiments, the present invention relates to any of the aforementioned polymers, wherein the redox-responsive moieties are ferrocenes.

In certain embodiments, the redox-responsive moieties comprise more than one metallocenes tethered together. For example, the metallocenyl group in a first subunit may comprise two or more metallocenyl groups linked together through an organic linking group. Furthermore, the cyclopentadienide ion(s) of the metallocenyl group may be bridged and/or substituted. Non-limiting examples of suitable substituents on the cyclopentadienide ion ring of metallocenyl groups include a silyl group, an alkyl group, an aryl group, an alkenyl group, and a part of a ring group, such as cycloalkyl groups, heterocyclic groups, or aryl groups (such as a benzo group). Non-limiting examples of suitable bridging group linking two cyclopentadienide ions together include a silylene group, an alkylene group, an arylene group, and combinations thereof. Furthermore, the metal ion of the metallocenyl group may bond to at least another anion or group such as hydride, halides, an alkyl group, an aryl group, or an alkene group.

In certain embodiments, the present invention relates to any of the aforementioned polymers, wherein the weight average molecular weight of the polymer is between about 1,000 amu and 1,000,000 amu. In certain embodiments, the present invention relates to any of the aforementioned polymers, wherein the number average molecular weight of the polymer is between about 1,000 amu and about 100,000 amu. In certain embodiments, the present invention relates to any of the aforementioned polymers, wherein the number average molecular weight of the polymer is between about 10,000 amu and about 100,000 amu. In certain embodiments, the present invention relates to any of the aforementioned polymers, wherein the number average molecular weight of the polymer is between about 1,000 amu and about 10,000 amu. In certain embodiments, the present invention relates to any of the aforementioned polymers, wherein the number average molecular weight of the polymer is between about 10,000 amu and about 50,000 amu. In certain embodiments, the present invention relates to any of the aforementioned polymers, wherein the number average molecular weight of the polymer is between about 50,000 amu and about 100,000 amu. In certain embodiments, the present invention relates to any of the aforementioned polymers, wherein the weight average molecular weight of the polymer is infinity.

In certain embodiments, the present invention relates to any of the aforementioned polymers, wherein the polymer is formed by the polymerization of unsaturated ethylenic-containing subunits or via an addition polymerization.

In certain embodiments, the present invention relates to any of the aforementioned polymers, further comprising a plurality of second subunits; and a plurality of third subunits; wherein the plurality of first subunits are represented by formula I:

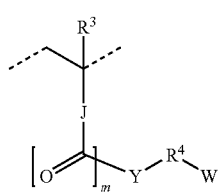

I the plurality of second subunits are represented by formula II:

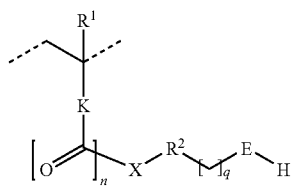

II and the plurality of third subunits are represented by formula III:

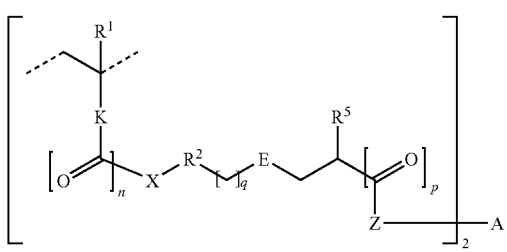

wherein, independently for each occurrence,
R is hydrogen or alkyl;
$R^1$ is hydrogen or alkyl;
K is absent, —O—, —S— or —N(R)—;
n is 0 or 1;
X is absent, —O—, —S— or —N(R)—;
$R^2$ is absent, alkylene, cycloalkylene, heterocyclylene, arylene, heteroarylene, cycloalkylalkylene, heterocyclylalkylene, arylalkylene or heteroarylalkylene;
q is 0-10 inclusive;
E is —O—, —S— or —N(R)—;
$R^3$ is hydrogen or alkyl;
J is absent, —O—, —S— or —N(R)—;
m is 0 or 1;
Y is absent, —O—, —S— or —N(R)—;
$R^4$ is absent or alkylene;
W is a redox-responsive moiety;
$R^5$ is hydrogen or alkyl;
Z is absent, —O—, —S— or —N(R)—
A is alkylene, arylene or heteroarylene; and
------ depicts a bond to a first subunit, a bond to a second subunit, a bond to a third subunit, a bond to a hydrogen atom, or a bond to a radical formed by the decomposition of an initiator, provided at least one ------ depicts a bond to a radical formed by the decomposition of an initiator.

In certain embodiments, the present invention relates to any of the aforementioned polymers, wherein R is hydrogen or methyl. In certain embodiments, the present invention relates to any of the aforementioned polymers, wherein R is hydrogen.

In certain embodiments, the present invention relates to any of the aforementioned polymers, wherein $R^1$ is hydrogen or methyl. In certain embodiments, the present invention relates to any of the aforementioned polymers, wherein $R^1$ is hydrogen. In certain embodiments, the present invention relates to any of the aforementioned polymers, wherein $R^1$ is methyl.

In certain embodiments, the present invention relates to any of the aforementioned polymers, wherein K is absent. In certain embodiments, the present invention relates to any of the aforementioned polymers, wherein K is —O—. In certain embodiments, the present invention relates to any of the aforementioned polymers, wherein K is —N(H)—.

In certain embodiments, the present invention relates to any of the aforementioned polymers, wherein n is 0. In certain embodiments, the present invention relates to any of the aforementioned polymers, wherein n is 1.

In certain embodiments, the present invention relates to any of the aforementioned polymers, wherein X is absent. In certain embodiments, the present invention relates to any of the aforementioned polymers, wherein X is —O—. In certain embodiments, the present invention relates to any of the aforementioned polymers, wherein X is —N(H)—.

In certain embodiments, the present invention relates to any of the aforementioned polymers, wherein $R^2$ is alkylene. In certain embodiments, the present invention relates to any of the aforementioned polymers, wherein $R^2$ is absent.

In certain embodiments, the present invention relates to any of the aforementioned polymers, wherein q is 0. In certain embodiments, the present invention relates to any of the aforementioned polymers, wherein q is 1. In certain embodiments, the present invention relates to any of the aforementioned polymers, wherein q is 2. In certain embodiments, the present invention relates to any of the aforementioned polymers, wherein q is 3. In certain embodiments, the present invention relates to any of the aforementioned polymers, wherein q is 4. In certain embodiments, the present invention relates to any of the aforementioned polymers, wherein q is 5. In certain embodiments, the present invention relates to any of the aforementioned polymers, wherein q is 6. In certain embodiments, the present invention relates to any of the aforementioned polymers, wherein q is 7. In certain embodiments, the present invention relates to any of the aforementioned polymers, wherein q is 8. In certain embodiments, the present invention relates to any of the aforementioned polymers, wherein q is 9. In certain embodiments, the present invention relates to any of the aforementioned polymers, wherein q is 10.

In certain embodiments, the present invention relates to any of the aforementioned polymers, wherein E is —O—. In certain embodiments, the present invention relates to any of the aforementioned polymers, wherein E is —N(H)—.

In certain embodiments, the present invention relates to any of the aforementioned polymers, wherein K is absent; n is 1; X is —O—; and $R^2$ is absent. In certain embodiments, the present invention relates to any of the aforementioned polymers, wherein K is absent; n is 1; X is —O—; $R^2$ is absent; and q is 4. In certain embodiments, the present invention relates to any of the aforementioned polymers, wherein K is absent; n is 1; X is —O—; $R^2$ is absent; q is 4; and E is —O—. In certain embodiments, the present invention relates to any of the aforementioned polymers, wherein $R^2$ is absent; q is 4; and E is —O—.

In certain embodiments, the present invention relates to any of the aforementioned polymers, wherein $R^3$ is hydrogen or methyl. In certain embodiments, the present invention relates to any of the aforementioned polymers, wherein $R^3$ is hydrogen. In certain embodiments, the present invention relates to any of the aforementioned polymers, wherein $R^3$ is methyl.

In certain embodiments, the present invention relates to any of the aforementioned polymers, wherein J is absent. In certain embodiments, the present invention relates to any of the aforementioned polymers, wherein J is —O—. In certain embodiments, the present invention relates to any of the aforementioned polymers, wherein J is —N(H)—.

In certain embodiments, the present invention relates to any of the aforementioned polymers, wherein m is 0. In certain embodiments, the present invention relates to any of the aforementioned polymers, wherein m is 1.

In certain embodiments, the present invention relates to any of the aforementioned polymers, wherein Y is absent. In certain embodiments, the present invention relates to any of the aforementioned polymers, wherein Y is —O—. In certain embodiments, the present invention relates to any of the aforementioned polymers, wherein Y is —N(H)—.

In certain embodiments, the present invention relates to any of the aforementioned polymers, wherein $R^4$ is absent. In certain embodiments, the present invention relates to any of the aforementioned polymers, wherein $R^4$ is alkylene.

In certain embodiments, the present invention relates to any of the aforementioned polymers, wherein W is metallocenyl. In certain embodiments, the present invention relates to any of the aforementioned polymers, wherein W is ferrocenyl, nickelocenyl, cobaltocenyl, zirconocenyl, ruthenocenyl, chromocenyl, hafnocenyl, titanocenyl, molybdenocenyl, niobocenyl, tungstenocenyl, or vanadocenenyl. In certain embodiments, the present invention relates to any of the aforementioned polymers, wherein W is ferrocenyl.

In certain embodiments, the present invention relates to any of the aforementioned polymers, wherein J is absent; n is 0; Y is absent; and $R^4$ is absent. In certain embodiments, the present invention relates to any of the aforementioned polymers, wherein J is absent; n is 0; Y is absent; $R^4$ is absent; and W is metallocenyl. In certain embodiments, the present invention relates to any of the aforementioned polymers, wherein J is absent; n is 0; Y is absent; $R^4$ is absent; and W is ferrocenyl. In certain embodiments, the present invention relates to any of the aforementioned polymers, wherein $R^4$ is absent; and W is ferrocenyl.

In certain embodiments, the present invention relates to any of the aforementioned polymers, wherein $R^5$ is hydrogen or methyl. In certain embodiments, the present invention relates to any of the aforementioned polymers, wherein $R^5$ is hydrogen. In certain embodiments, the present invention relates to any of the aforementioned polymers, wherein $R^5$ is methyl.

In certain embodiments, the present invention relates to any of the aforementioned polymers, wherein p is 0. In certain embodiments, the present invention relates to any of the aforementioned polymers, wherein p is 1.

In certain embodiments, the present invention relates to any of the aforementioned polymers, wherein Z is —O—. In certain embodiments, the present invention relates to any of the aforementioned polymers, wherein Z is —N(H)—.

In certain embodiments, the present invention relates to any of the aforementioned polymers, wherein A is alkylene. In certain embodiments, the present invention relates to any of the aforementioned polymers, wherein A is $C_1$-$C_4$ alkylene. In certain embodiments, the present invention relates to any of the aforementioned polymers, wherein A is methylene. In certain embodiments, the present invention relates to any of the aforementioned polymers, wherein A is ethylene.

In certain embodiments, the present invention relates to any of the aforementioned polymers, wherein the radical formed by the decomposition of an initiator is halo, alkyl, cyanoalkyl, cycloalkyl, aryl, heteroaryl, aralkyl, heteroaralkyl, alkyloxy, cycloalkyloxy, aryloxy, heteroaryloxy, aralkyloxy, heteroaralkyloxy, alkylcarbonyoxy, cycloalkylcarbonyoxy, arylcarbonyoxy, heteroarylcarbonyoxy, aralkylcarbonyoxy, or heteroaralkylcarbonyoxy.

In certain embodiments, the present invention relates to any of the aforementioned polymers, wherein the radical formed by the decomposition of an initiator is —C(CH$_3$)$_2$C≡N.

In certain embodiments, the present invention relates to any of the aforementioned polymers, wherein the radical formed by the decomposition of an initiator is —OC(=O)Ph.

In certain embodiments, the present invention relates to any of the aforementioned polymers, wherein the radical formed by the decomposition of an initiator is tethered to a solid support.

In certain embodiments, the present invention relates to any of the aforementioned polymers, wherein the solid support is carbon particles or carbon fibers.

In certain embodiments, the present invention relates to any of the aforementioned polymers, further comprising a plurality of second subunits; wherein the plurality of first subunits are represented by formula IV:

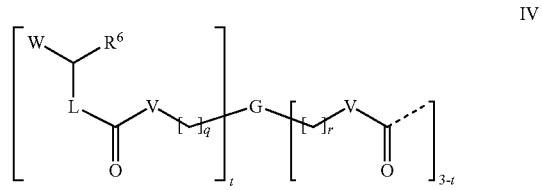

and the plurality of second subunits are represented by formula V:

wherein, independently for each occurrence,
W is a redox-responsive moiety;
$R^6$ is hydrogen or alkyl;
L is —O—, —S— or —N(H)—;
V is absent or —N(H)—;
q is 0, 1, 2, 3, 4, 5, 6, 7, 8, 9 r 10;
t is 1 or 2, provided that at least two occurrences of t are 2;
G is a alktriyl, cycloalktriyl, heterocycltriyl, artriyl, or heteroartriyl;
s is 0-50 inclusive;
U is —O—, —S— or —N($R^6$)—;
T is alkylene; and
------ depicts a bond between a first subunit and a second subunit, or, when ------ is connected to a U, ------ may be hydrogen.

In certain embodiments, the present invention relates to any of the aforementioned polymers, wherein W is metallocenyl. In certain embodiments, the present invention relates to any of the aforementioned polymers, wherein W is ferrocenyl, nickelocenyl, cobaltocenyl, zirconocenyl, ruthenocenyl, chromocenyl, hafnocenyl, titanocenyl, molybdenocenyl, niobocenyl, tungstenocenyl, or vanadocenenyl. In certain embodiments, the present invention relates to any of the aforementioned polymers, wherein W is ferrocenyl.

In certain embodiments, the present invention relates to any of the aforementioned polymers, wherein $R^6$ is hydrogen. In certain embodiments, the present invention relates to any of the aforementioned polymers, wherein $R^6$ is alkyl. In certain embodiments, the present invention relates to any of the aforementioned polymers, wherein $R^6$ is methyl.

In certain embodiments, the present invention relates to any of the aforementioned polymers, wherein L is —O—. In certain embodiments, the present invention relates to any of the aforementioned polymers, wherein L is —N(H)—.

In certain embodiments, the present invention relates to any of the aforementioned polymers, wherein V is —O—. In certain embodiments, the present invention relates to any of the aforementioned polymers, wherein V is —N(H)—.

In certain embodiments, the present invention relates to any of the aforementioned polymers, wherein q is 5. In certain embodiments, the present invention relates to any of the aforementioned polymers, wherein q is 6. In certain embodiments, the present invention relates to any of the aforementioned polymers, wherein q is 7.

In certain embodiments, the present invention relates to any of the aforementioned polymers, wherein G is heterocycltriyl. In certain embodiments, the present invention relates to any of the aforementioned polymers, wherein G is the triradical of 1,3,5-triazinane-2,4,6-trione.

In certain embodiments, the present invention relates to any of the aforementioned polymers, wherein U is —O—. In certain embodiments, the present invention relates to any of the aforementioned polymers, wherein U is —N(H)—.

In certain embodiments, the present invention relates to any of the aforementioned polymers, wherein T is $C_3$-$C_5$ alkylene. In certain embodiments, the present invention relates to any of the aforementioned polymers, wherein T is —CH$_2$CH$_2$CH$_2$CH$_2$—.

In certain embodiments, the present invention relates to any of the aforementioned polymers, wherein s is 6, 7 or 8. In certain embodiments, the present invention relates to any of the aforementioned polymers, wherein s is 13, 14 or 15. In certain embodiments, the present invention relates to any of the aforementioned polymers, wherein s is 26, 27 or 28.

In certain embodiments, the present invention relates to any of the aforementioned polymers, wherein W is ferrocenyl; and L is O. In certain embodiments, the present invention relates to any of the aforementioned polymers, wherein W is ferrocenyl; L is O; $R^6$ is methyl.

In certain embodiments, the present invention relates to any of the aforementioned polymers, wherein V is —N(H)—; q is 6; and G is heterocycltricyl. In certain embodiments, the present invention relates to any of the aforementioned polymers, wherein V is —N(H)—; q is 6; and G is the triradical of 1,3,5-triazinane-2,4,6-trione.

In certain embodiments, the present invention relates to any of the aforementioned polymers, wherein U is —O—; and T is —CH$_2$CH$_2$CH$_2$CH$_2$—. In certain embodiments, the present invention relates to any of the aforementioned polymers, wherein U is —O—; T is —CH$_2$CH$_2$CH$_2$CH$_2$—; and s is 5-15 inclusive. In certain embodiments, the present invention relates to any of the aforementioned polymers, wherein U is —O—; T is —CH$_2$CH$_2$CH$_2$CH$_2$—; and s is 16-30 inclusive.

In certain embodiments, the present invention relates to any of the aforementioned polymers, wherein the polymer comprises about 5 mol % of the first subunit (e.g., a subunit of formula I or formula IV). In certain embodiments, the present invention relates to any of the aforementioned polymers, wherein the polymer comprises about 10 mol % of the first subunit. In certain embodiments, the present invention relates to any of the aforementioned polymers, wherein the polymer comprises about 15 mol % of the first subunit. In certain embodiments, the present invention relates to any of the aforementioned polymers, wherein the polymer comprises about 20 mol % of the first subunit. In certain embodiments, the present invention relates to any of the aforementioned polymers, wherein the polymer comprises about 25 mol % of the first subunit. In certain embodiments, the present invention relates to any of the aforementioned polymers, wherein the polymer comprises about 30 mol % of the first subunit. In certain embodiments, the present invention relates to any of the aforementioned polymers, wherein the polymer comprises about 35 mol % of the first subunit. In certain embodiments, the present invention relates to any of the aforementioned polymers, wherein the polymer comprises about 40 mol % of the first subunit. In certain embodiments, the present invention relates to any of the aforementioned polymers, wherein the polymer comprises about 45 mol % of the first subunit. In certain embodiments, the present invention relates to any of the aforementioned polymers, wherein the polymer comprises about 50 mol % of the first subunit.

In certain embodiments, the present invention relates to any of the aforementioned polymers, wherein the polymer comprises at least about 5 mol % of the first subunit. In certain embodiments, the present invention relates to any of the aforementioned polymers, wherein the polymer comprises at least about 10 mol % of the first subunit. In certain embodiments, the present invention relates to any of the aforementioned polymers, wherein the polymer comprises at least about 15 mol % of the first subunit. In certain embodiments, the present invention relates to any of the aforementioned polymers, wherein the polymer comprises at least about 20 mol % of the first subunit. In certain embodiments, the present invention relates to any of the aforementioned polymers, wherein the polymer comprises at least about 25 mol % of the first subunit. In certain embodiments, the present invention relates to any of the aforementioned polymers, wherein the polymer comprises at least about 30 mol % of the first subunit. In certain embodiments, the present invention relates to any of the aforementioned polymers, wherein the polymer comprises at least about 35 mol % of the first subunit. In certain embodiments, the present invention relates to any of the aforementioned polymers, wherein the polymer comprises at least about 40 mol % of the first subunit. In certain embodiments, the present invention relates to any of the aforementioned polymers, wherein the polymer comprises at least about 45 mol % of the first subunit. In certain embodiments, the present invention relates to any of the aforementioned polymers, wherein the polymer comprises at least about 50 mol % of the first subunit.

In certain embodiments, the present invention relates to any of the aforementioned polymers, wherein the polymer comprises less than about 5 mol % of the first subunit. In certain embodiments, the present invention relates to any of the aforementioned polymers, wherein the polymer comprises less than about 10 mol % of the first subunit. In certain embodiments, the present invention relates to any of the aforementioned polymers, wherein the polymer comprises less than about 15 mol % of the first subunit. In certain embodiments, the present invention relates to any of the aforementioned polymers, wherein the polymer comprises less than about 20 mol % of the first subunit. In certain embodiments, the present invention relates to any of the aforementioned polymers, wherein the polymer comprises less than about 25 mol % of the first subunit. In certain embodiments, the present invention relates to any of the aforementioned polymers, wherein the polymer comprises less than about 30 mol % of the first subunit. In certain embodiments, the present invention relates to any of the aforementioned polymers, wherein the polymer comprises less than about 35 mol % of the first subunit. In certain embodiments, the present invention relates to any of the aforementioned polymers, wherein the polymer comprises less than about 40 mol % of the first subunit. In certain embodiments, the present invention relates to any of the aforementioned polymers, wherein the polymer comprises less than about 45 mol % of the first subunit. In certain embodiments, the present invention relates to any of the aforementioned polymers, wherein the polymer comprises less than about 50 mol % of the first subunit.

In certain embodiments, the present invention relates to any of the aforementioned polymers, wherein the polymer comprises between about 1 mol % and about 50 mol % of the first subunit. In certain embodiments, the present invention relates to any of the aforementioned polymers, wherein the polymer comprises between about 10 mol % and about 45 mol % of the first subunit. In certain embodiments, the present invention relates to any of the aforementioned polymers, wherein the polymer comprises between about 15 mol % and about 30 mol % of the first subunit.

Polymerization Processes and Selected Polymers Produced Thereby

The polymerization process for preparing polymer may be any suitable polymerization process. Examples of suitable polymerization processes include radical polymerization, cationic polymerization, bulk polymerization, reverse suspension-polymerization, spray-polymerization, condensation polymerization, and combinations thereof. In certain embodiments, the polymerization process is bulk polymerization.

The polymerization temperatures may be any temperature from below room temperature (such as 0° C. or below) to about 100° C., or even above about 100° C. depending on the monomers, initiators and solvents used as is known to those skilled in the art.

If necessary, the polymerization procedure may require the exclusion of water or any other nucleophiles, as commonly known for cationic polymerization of vinyl ethers and is known to those skilled in the art of cationic and living cationic polymerization.

If necessary, the polymerization procedure may require the exclusion of oxygen or any other radical quencher, as commonly known in the art of free-radical or living free-radical polymerization.

One aspect of the invention relates to a polymer obtained by a polymerization process, as well as the polymerization process itself, which polymerization process comprises polymerizing a polymerization mixture, wherein the polymerization mixture comprises:

a di-functional redox-reactive compound; and
a di-functional spacer compound.

In certain embodiments, the present invention relates to any of the aforementioned polymers obtained by a polymerization process, wherein the di-functional redox-reactive compound is a di-functional metallocene. In certain embodiments, the present invention relates to any of the aforementioned polymers obtained by a polymerization process, wherein the di-functional redox-reactive compound is a di-functional ferrocene (such as a vinyl ferrocene, ferrocene diol, a ferrocene dialdehyde, a ferrocene diamine, a ferrocene diisocyanate, or a ferrocene dicarboxylic acid).

In certain embodiments, the present invention relates to any of the aforementioned polymers obtained by a polymerization process, wherein the di-functional spacer compound is an organic diol (such as ethylene glycol, 1,6-hexane diol, polyalkylene oxides, glycols, poly(ethylene) oxide, as well as like diols and polyols).

In certain embodiments, the present invention relates to any of the aforementioned polymers obtained by a polymerization process, wherein the polymerization process can be accomplished by, for example, heating about 1 molar equivalent of the di-functional redox-reactive compound, about 1 to about 2 molar equivalents of the di-functional spacer compound, and optionally an isocyanate, in a suitable organic medium, such as tetrahydrofuran, dioxane, dimethylformamide and other organic solvents or combinations thereof.

In certain embodiments, the present invention relates to any of the aforementioned polymers obtained by a polymerization process, wherein the polymerization mixture further comprises a catalyst. In certain embodiments, the present invention relates to any of the aforementioned polymers obtained by a polymerization process, wherein the polymerization mixture further comprises an organic acid catalyst. In certain embodiments, the present invention relates to any of the aforementioned polymers obtained by a polymerization process, wherein the polymerization mixture further comprises an organic acid catalyst selected from the group consisting of para-toluene sulfonic acid (p-TSA) and like protic acids.

In certain embodiments, the present invention relates to any of the aforementioned polymers obtained by a polymerization process, wherein the polymerization mixture further comprises a multifunctional isocyanate. In certain embodiments, the present invention relates to any of the aforementioned polymers obtained by a polymerization process, wherein the polymerization mixture further comprises an initiator.

Another aspect of the invention relates to a polymer obtained by a polymerization process, as well as the polymerization process itself, which polymerization process comprises polymerizing a polymerization mixture, wherein the polymerization mixture comprises:

a di-functional redox-reactive compound; and
a multifunctional isocyanate.

In certain embodiments, the present invention relates to any of the aforementioned polymers obtained by a polymerization process wherein the polymers include pendant groups selected from the group consisting of alkyl groups, alkenyl groups, alkynyl groups, aryl groups, alkoxy groups, aryloxy groups, halogen atoms, amino groups, alkylamino groups, arylamino groups, a carboxyl group, alkoxycarbonyl groups, a sulfo group, a nitro group, a cyano group, an amido group, alkylsulfonyl groups, arylsulfonyl groups and so on.

In certain embodiments, the present invention relates to any of the aforementioned polymers obtained by a polymerization process, wherein the multifunctional isocyanate is a diisocyanates. In certain embodiments, the present invention relates to any of the aforementioned polymers obtained by a polymerization process, wherein the diisocyanate is selected from the group consisting of aromatic diisocyanate compounds such as 2,4-tolylene diisocyanate, 2,4-tolylene diisocyanate dimer, 2,6-tolylene diisocyanate, p-xylylene diisocyanate, m-xylylene diisocyanate, 4,4'-diphenylmethane diisocyanate, 1,5-naphthylene diisocyanate and 3,3'-dimethylbiphenyl-4,4'-diisocyanate; aliphatic diisocyanate compounds such as hexamethylene diisocyanate, trimethylhexamethylene diisocyanate, lysine diisocyanate and dimeric acid diisocyanate; alicyclic diisocyanate compounds such as isophorone diisocyanate, 4,4'-methylenebis(cyclohexyl isocyanate), methylcyclohexane-2,4-diisocyanate, methylcyclohexane-2,6-diisocyanate and 1,3-(isocyanomethyl)cyclohexane; and diisocyanate compounds obtained as the product of a reaction between a diol and a diisocyanate such as an adduct of 1 mole of 1,3-butylene glycol and 2 moles of tolylene diisocyanate. In addition, diisocyanate compounds comprising an unsaturated group, obtained by addition-reacting a triisocyanate compound with one equivalent of a monofunctional alcohol or a monofunctional amine compound having an unsaturated group, may be used.

In certain embodiments, the present invention relates to any of the aforementioned polymers obtained by a polymerization process, wherein the multifunctional isocyanate is a triisocyanate.

In certain embodiments, the present invention relates to any of the aforementioned polymers obtained by a polymerization process, wherein the polymerization mixture further comprises a diol.

In certain embodiments, the present invention relates to any of the aforementioned polymers obtained by a polymerization process, wherein the polymerization mixture further comprises a diol; wherein the diol is selected from the group consisting of commercially-available diols, such as trimethylolpropane monoallyl ether, as well as compounds which can be easily produced by reacting a halogenated diol compound, a triol compound or an aminodiol compound with a carboxylic acid, an acid chloride, an isocyanate, an alcohol, an amine, a thiol or a halogenated alkyl compound having an unsaturated group.

In certain embodiments, the present invention relates to any of the aforementioned polymers obtained by a polymerization process, wherein the polymerization mixture further comprises a diol selected from the group consisting of polyether diol compounds, polyester diol compounds and polycarbonate diol compounds.

In certain embodiments, the present invention relates to any of the aforementioned polymers obtained by a polymerization process, wherein the polymerization mixture further comprises a diol selected from the group consisting of ethylene glycol, diethylene glycol, triethylene glycol, tetraethylene glycol, propylene glycol, dipropylene glycol, polyethylene glycol, polypropyleneglycol, neopentyl glycol, 1,3-butylene glycol, 1,6-hexanediol, 2-butene-1,4-diol, 2,2,4-trimethyl-1,3-pentexadiol, 1,4-bis-.beta.-hydroxyethoxycyclohexane, cyclohexanedimethanol, tricyclodecanedimethanol, hydrogenated bisphenol A, hydrogenated bisphenol F, ethylene oxide adducts of bisphenol A, propylene oxide adducts of bisphenol A, ethylene oxide adducts of bisphenol F, propylene oxide adducts of bisphenol A, ethylene oxide adducts of hydrogenated bisphenol A, propylene oxide adducts of hydrogenated bisphenol A, hydroquinonedihydroxyethyl ether, p-xylylene glycol, dihydroxyethylsulfone, bis(2-hydroxyethyl)-2,4-tolylenedicarbamate, 2,4-tolylene-bis(2-hydroxyethylcarbamide), bis(2-hydroxyethyl)-m-xylylenedicarbamate and bis(2-hydroxyethyl) isophthalate.

In certain embodiments, the present invention relates to any of the aforementioned polymers obtained by a polymerization process, wherein the polymerization mixture further comprises a diol selected from the group consisting of as ethylene glycol, diethylene glycol, triethylene glycol, tetraethylene glycol, propylene glycol, dipropylene glycol, polyethylene glycol, polypropylene glycol, neopentyl glycol, 1,3-butylene glycol, 1,6-heanediol, 2-butene-1,4-diol, 2,2,4-trimethyl-1,3-pentanediol, 1,4-bis-.beta.-hydroxyethoxycyclohexane, cyclohexane dimethanol, tricyclodecane dimethanol, hydrogenated bisphenol A, hydrogenated bisphenol F, ethylene oxide adduct of bisphenol A, propylene oxide adduct of bisphenol A, ethylene oxide adduct of bis phenol F, propylene oxide adduct of bisphenol F, ethylene oxide adduct of hydrogenated bisphenol A, propylene oxide adduct of hydrogenated bisphenol A, hydroquinone dihydroxy ethyl ether, p-xylylene glycol, dihydroxyethyl sulfone, bis(2-hydroxyethyl)-2,4-tolylene dicarbamate, 2,4-tolylene-bis(2-hydroxyethylcarbamide), bis(2-hydroxyethyl)-m-xylylene dicarbamate, bis(2-hydroxyethyl) isophthalate, 1,3-propanediol, 1,4-butanediol, 1,5-pentanediol, 1,6-hexanediol, 1,7-heptanediol, 1,8-octanediol, 2-butene-1,4-diol, cis-2-butene-1,4-diol, trans-2-butene-1,4-diol, catechol, resorcin, hydroquinone, 4-methylcatechol, 4-t-butylcatechol, 4-acetylcatechol, 3-methoxycatechol, 4-phenylcatechol, 4-methylresorcin, 4-ethylresorcin, 4-t-butylresorcin, 4-hexylresorcin, 4-chlororesorcin, 4-benzylresorcin, 4-acetylresorcin, 4-carbomethoxyresorcin, 2-methylresorcin, 5-methylresorcin, t-butylhydroquinone, 2,5-d-t-butylhydroquinone, 2,5-di-t-amylhydroquinone, tetramethylhydroquinone, tetrachlorohydroquinone, methylcarboaminohydroquinone, methylureidohydroquinone, methylthiohydroquinone, benzonorbornene-3,6-diol, bisphenol A, bisphenol S, 3,3'-dichlorobisphenol S, 4,4'-dihydroxybenzophenone, 4,4'-dihydroxybiphenyl, 4,4'-thiodiphenol, 2,2'-dihydroxydiphenylmethane, 3,4-bis(p-hydroxyphenyl)hexane, 1,4-bis(2-(hydroxyphenyl)propyl) benzene, bis(4-hydroxyphenyl)methylamine, 1,3-dihydroxynaphthalene, 1,4-dihydroxynaphthalene, 1,5-dihydroxynaphthalene, 2,6-dihydroxynaphthalene, 1,5-dihydroxyanthraquinone, 2-hydroxybenzyl alcohol, 4-hydroxybenzyl alcohol, 2-hydroxy-3,5-di-t-butylbenzyl alcohol, 4-hydroxy-3,5-di-t-butylbenzyl alcohol, 4-hydroxyphenethyl alcohol, 2-hydroxyethyl-4-hydroxybenzoate, 2-hydroxyethyl-4-hydroxyphenyl acetate, resorcin mono-2-hydroxyethyl ether, diethylene glycol, triethylene glycol, tetraethylene glycol, pentaethylene glycol, hexaethylene glycol, heptaethylene glycol, octaethylene glycol, di-1,2-propylene glycol, tri-1,2-propylene glycol, tetra-1,2-propylene glycol, hexa-1,2-propylene glycol, di-1,3-propylene glycol, tri-1,3-propylene glycol, tetra-1,3-propylene glycol, di-1,3-butylene glycol, tri-1,3-butylene glycol, hexa-1,3-butylene glycol, polyethylene glycol having a weight-average molecular weight of 1000, polyethylene glycol having a weight-average molecular weight of 1500, polyethylene glycol having a weight-average molecular weight of 2000, polyethylene glycol having a weight-average molecular weight of 3000, polyethylene glycol having a weight-average molecular weight of 7500, polypropylene glycol having a weight-average molecular weight of 400, polypropylene glycol having a weight-average molecular weight of 700, polypropylene glycol having a weight-average molecular weight of 1000, polypropylene glycol having a weight-average molecular weight of 2000, polypropylene glycol having a weight-average molecular weight of 3000, polypropylene glycol having a weight-average molecular weight of 4000.

In certain embodiments, the present invention relates to any of the aforementioned polymers obtained by a polymerization process, wherein the polymerization mixture further comprises a diol compound having a carboxyl group (such as 3,5-dihydroxybenzoic acid, 2,2-bis(hydroxymethyl)propionic acid, 2,2-bis(2-hydroxyethyl)propionic acid, 2,2-bis(3-hydorxydipropyl)propionic acid, bishydroxymethyl)acetic acid, bis(4-hydroxyphenyl)acetic acid, 2,2-bis(hydroxymethyl)butyric acid, 4,4-bis(4-hydroxyphenyl)pentanoic acid, tartaric acid, N,N-dihydroxyethylglycine and N,N-bis(2-hydroxyethyl)-3-carboxy-propionamide).

To impart an affinity toward certain alcohols, in certain embodiments, the polyols described herein may be partially or completely esterified with one carboxylic acid or with different unsaturated carboxylic acids, and in partial esters the free hydroxyl groups may be modified, for example etherified or esterified with other carboxylic acids.

Examples of esters include trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bis-acrylates and bismethacrylates of polyethylene glycol with a weight-average molecular weight of from about 200 amu to 1500 amu, or mixtures thereof.

In certain embodiments, the present invention relates to any of the aforementioned polymers obtained by a polymerization process, wherein the polymerization mixture further comprises a diamine. In certain embodiments, the present invention relates to any of the aforementioned polymers obtained by a polymerization process, wherein the polymerization mixture further comprises an aliphatic diamine (such as ethylenediamine, propylenediamine, tetramethylenediamine, pentamethylenediamine, hexamethylenediamine, heptamethylenediamine, octamethylenediamine, dodecamethylenediamine, propane-1,2-diamine, bis(3-aminopropyl)methylamine, 1,3-bis(3-aminopropy)tetramethylsiloxane, piperazine, 2,5-dimethylpiperazine, N-(2-aminoethyl)piperazine, 4-amino-2,2-6,6-tetramethylpiperidine, N,N-dimethylethylenediamine, lysine, L-cysteine and isophoronediamine; aromatic diamine compounds such as o-phenylenediamine, m-phenylenediamine, p-phenylenediamine, 2,4-tolylenediamine, benzidine, o-ditolydine, o-dianinsidine, 4-nitrom-phenylenediamine, 2,5-dimethoxy-p-phenylenediamine, bis(4-aminophenyl)sulfone, 4-carboxyphonylenediamine, 3-carboxy-m-phenylenediamine, 4,4'-diaminophenyl ether and 1,8-naphthalenediamine; heterocyclic amine compounds such as 2-aminoimidazole, 3-aminotriazole, 5-amino-1H-tetrazole, 4-aminopyrazole, 2-aminobenzimidazole, 2-amine-5-carbxy-triazole, 2,4-diamino-6-methyl-s-triazine, 2,6-diaminopyridine, L-histidine, DL-tryptophan and adenine; and aminoalcohol or aminophenol compounds such as ethanolamine, N-methylethanolamine, N-ethylethanolamine, 1-amino-2-propanol, 1-amino-3-propanol, 2-aminoethoxyethanol, 2-aminothioethoxyethanol, 2-amino-2-methyl-1-propanol; p-aminophenol, m-aminophenol, o-aminophenol, 4-methyl-2-aminophenol, 2-chloro-4-aminophenol, 4-methoxy-3-aminophenol, 4-hydroxybenzylamine, 4-amino-1-naphthol, 4-aminosalicylic acid, 4-hydroxy-N-phenyglycine, 2-aminobenzyl alcohol, 4-aminophenethyl alcohol, 2-carboxy-5-amino-1-naphthol and L-tyrosine).

Another aspect of the invention relates to a polymer obtained by a polymerization process, as well as the polymerization process itself, which polymerization process comprises polymerizing a polymerization mixture, wherein the polymerization mixture comprises a plurality of a first monomer represented by formula VI, or a monomer equivalent thereof:

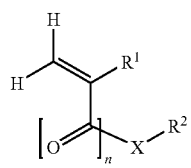

VI a plurality of second monomer represented by formula VII, or a monomer equivalent thereof:

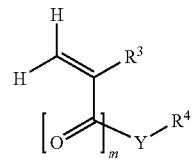

VII and a plurality of a crosslinker represented by formula VIII:

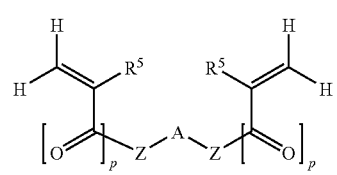

VIII wherein, independently for each occurrence,
R is hydrogen or alkyl;
$R^1$ is hydrogen or alkyl;
$R^2$ is alkyl, cycloalkyl, heterocyclyl, aryl, heteroaryl, cycloalkylalkyl, heterocyclylalkyl, arylalkyl or heteroarylalkyl, which is substituted with at least one —$(CH_2)_q$E-H;
q is 0, 1, 2, 3, 4, or 5;
E is —O—, —S— or —N(R)—;
X is absent, —O—, —S— or —N(R)—;
n is 0 or 1;
$R^3$ is hydrogen or alkyl;
$R^4$ is W or alkyl substituted with at least one W;
W is a redox-responsive moiety;
Y is absent, —O—, —S— or —N(R)—;
m is 0 or 1;
$R^5$ is hydrogen or alkyl;
Z is absent, —O—, —S— or —N(R)—; and
A is alkylene, arylene or heteroarylene.

In certain embodiments, the present invention relates to any of the aforementioned polymers obtained by a polymerization process, wherein R is hydrogen or methyl. In certain embodiments, the present invention relates to any of the aforementioned polymers obtained by a polymerization process, wherein R is hydrogen. In certain embodiments, the present invention relates to any of the aforementioned polymers obtained by a polymerization process, wherein R is methyl.

In certain embodiments, the present invention relates to any of the aforementioned polymers obtained by a polymerization process, wherein $R^1$ is hydrogen or methyl. In certain embodiments, the present invention relates to any of the aforementioned polymers obtained by a polymerization process, wherein $R^1$ is hydrogen.

In certain embodiments, the present invention relates to any of the aforementioned polymers obtained by a polymerization process, wherein n is 0. In certain embodiments, the present invention relates to any of the aforementioned polymers obtained by a polymerization process, wherein n is 1.

In certain embodiments, the present invention relates to any of the aforementioned polymers obtained by a polymerization process, wherein X is —O—.

In certain embodiments, the present invention relates to any of the aforementioned polymers obtained by a polymerization process, wherein q is 0 or 1. In certain embodiments, the present invention relates to any of the aforementioned polymers obtained by a polymerization process, wherein q is 0. In certain embodiments, the present invention relates to any of the aforementioned polymers obtained by a polymerization process, wherein q is 1.

In certain embodiments, the present invention relates to any of the aforementioned polymers obtained by a polymerization process, wherein E is hydroxyl.

In certain embodiments, the present invention relates to any of the aforementioned polymers obtained by a polymerization process, wherein $R^3$ is hydrogen or methyl. In certain embodiments, the present invention relates to any of the aforementioned polymers obtained by a polymerization process, wherein $R^3$ is hydrogen.

In certain embodiments, the present invention relates to any of the aforementioned polymers obtained by a polymerization process, wherein m is 0. In certain embodiments, the present invention relates to any of the aforementioned polymers obtained by a polymerization process, wherein m is 1.

In certain embodiments, the present invention relates to any of the aforementioned polymers obtained by a polymerization process, wherein Y is absent.

In certain embodiments, the present invention relates to any of the aforementioned polymers obtained by a polymerization process, wherein $R^4$ is W.

In certain embodiments, the present invention relates to any of the aforementioned polymers, wherein W is metallocenyl. In certain embodiments, the present invention relates to any of the aforementioned polymers, wherein W is ferrocenyl, nickelocenyl, cobaltocenyl, zirconocenyl, ruthenocenyl, chromocenyl, hafnocenyl, titanocenyl, molybdenocenyl, niobocenyl, tungstenocenyl, or vanadocenenyl. In certain embodiments, the present invention relates to any of the aforementioned polymers, wherein W is ferrocenyl.

In certain embodiments, the present invention relates to any of the aforementioned polymers obtained by a polymerization process, wherein $R^5$ is hydrogen or methyl. In certain embodiments, the present invention relates to any of the aforementioned polymers obtained by a polymerization process, wherein $R^5$ is hydrogen. In certain embodiments, the present invention relates to any of the aforementioned polymers obtained by a polymerization process, wherein $R^5$ is methyl.

In certain embodiments, the present invention relates to any of the aforementioned polymers obtained by a polymerization process, wherein p is 0. In certain embodiments, the present invention relates to any of the aforementioned polymers obtained by a polymerization process, wherein p is 1.

In certain embodiments, the present invention relates to any of the aforementioned polymers obtained by a polymerization process, wherein Z is —O—. In certain embodiments, the present invention relates to any of the aforementioned polymers obtained by a polymerization process, wherein Z is —N(H)—.

In certain embodiments, the present invention relates to any of the aforementioned polymers obtained by a polymerization process, wherein A is alkylene. In certain embodiments, the present invention relates to any of the aforementioned polymers obtained by a polymerization process, wherein A is methylene, ethylene, propylene, or butylene. In certain embodiments, the present invention relates to any of the aforementioned polymers obtained by a polymerization process, wherein A is methylene. In certain embodiments, the present invention relates to any of the aforementioned polymers obtained by a polymerization process, wherein A is ethylene.

In certain embodiments, the present invention relates to any of the aforementioned polymers obtained by a polymerization process, wherein said polymerization mixture further comprises an initiator.

In certain embodiments, the present invention relates to any of the aforementioned polymers obtained by a polymerization process, wherein said polymerization mixture further comprises an initiator; and said initiator is added to said polymerization mixture via sequential addition.

In certain embodiments, the present invention relates to any of the aforementioned polymers obtained by a polymerization process, wherein the initiator is azoisobutyronitrile.

In certain embodiments, the present invention relates to any of the aforementioned polymers obtained by a polymerization process, wherein polymerization mixture comprises greater than about 50 mol % of the monomer represented by formula VI. In certain embodiments, the present invention relates to any of the aforementioned polymers obtained by a polymerization process, wherein polymerization mixture comprises greater than about 55 mol % of the monomer represented by formula VI. In certain embodiments, the present invention relates to any of the aforementioned polymers obtained by a polymerization process, wherein polymerization mixture comprises greater than about 60 mol % of the monomer represented by formula VI. In certain embodiments, the present invention relates to any of the aforementioned polymers obtained by a polymerization process, wherein polymerization mixture comprises greater than about 65 mol % of the monomer represented by formula VI. In certain embodiments, the present invention relates to any of the aforementioned polymers obtained by a polymerization process, wherein polymerization mixture comprises greater than about 70 mol % of the monomer represented by formula VI. In certain embodiments, the present invention relates to any of the aforementioned polymers obtained by a polymerization process, wherein polymerization mixture comprises greater than about 75 mol % of the monomer represented by formula VI. In certain embodiments, the present invention relates to any of the aforementioned polymers obtained by a polymerization process, wherein polymerization mixture comprises greater than about 80 mol % of the monomer represented by formula VI. In certain embodiments, the present invention relates to any of the aforementioned polymers obtained by a polymerization process, wherein polymerization mixture comprises greater than about 85 mol % of the monomer represented by formula VI. In certain embodiments, the present invention relates to any of the aforementioned polymers obtained by a polymerization process, wherein polymerization mixture comprises greater than about 90 mol % of the monomer represented by formula VI. In certain embodiments, the present invention relates to any of the aforementioned polymers obtained by a polymerization process, wherein polymerization mixture comprises greater than about 95 mol % of the monomer represented by formula VI.

In certain embodiments, the present invention relates to any of the aforementioned polymers obtained by a polymerization process, wherein polymerization mixture comprises between about 60 mol % and about 80 mol % of the monomer represented by formula VI. In certain embodiments, the present invention relates to any of the aforementioned polymers obtained by a polymerization process, wherein polymerization mixture comprises between about 70 mol % and about 90 mol % of the monomer represented by formula VI.

In certain embodiments, the present invention relates to any of the aforementioned polymers obtained by a polymerization process, wherein polymerization mixture comprises about 50 mol % of the monomer represented by formula VI.

In certain embodiments, the present invention relates to any of the aforementioned polymers obtained by a polymerization process, wherein polymerization mixture comprises about 55 mol % of the monomer represented by formula VI. In certain embodiments, the present invention relates to any of the aforementioned polymers obtained by a polymerization process, wherein polymerization mixture comprises about 60 mol % of the monomer represented by formula VI. In certain embodiments, the present invention relates to any of the aforementioned polymers obtained by a polymerization process, wherein polymerization mixture comprises about 65 mol % of the monomer represented by formula VI. In certain embodiments, the present invention relates to any of the aforementioned polymers obtained by a polymerization process, wherein polymerization mixture comprises about 70 mol % of the monomer represented by formula VI. In certain embodiments, the present invention relates to any of the aforementioned polymers obtained by a polymerization process, wherein polymerization mixture comprises about 75 mol % of the monomer represented by formula VI. In certain embodiments, the present invention relates to any of the aforementioned polymers obtained by a polymerization process, wherein polymerization mixture comprises about 80 mol % of the monomer represented by formula VI. In certain embodiments, the present invention relates to any of the aforementioned polymers obtained by a polymerization process, wherein polymerization mixture comprises about 85 mol % of the monomer represented by formula VI. In certain embodiments, the present invention relates to any of the aforementioned polymers obtained by a polymerization process, wherein polymerization mixture comprises about 90 mol % of the monomer represented by formula VI. In certain embodiments, the present invention relates to any of the aforementioned polymers obtained by a polymerization process, wherein polymerization mixture comprises about 95 mol % of the monomer represented by formula VI.

In certain embodiments, the present invention relates to any of the aforementioned polymers obtained by a polymerization process, wherein polymerization mixture comprises between about 1 mol % and about 50 mol % of the monomer represented by formula VII. In certain embodiments, the present invention relates to any of the aforementioned polymers obtained by a polymerization process, wherein polymerization mixture comprises between about 5 mol % and about 40 mol % of the monomer represented by formula VII. In certain embodiments, the present invention relates to any of the aforementioned polymers obtained by a polymerization process, wherein polymerization mixture comprises between about 10 mol % and about 30 mol % of the monomer represented by formula VII. In certain embodiments, the present invention relates to any of the aforementioned polymers obtained by a polymerization process, wherein polymerization mixture comprises between about 15 mol % and about 25 mol % of the monomer represented by formula VII. In certain embodiments, the present invention relates to any of the aforementioned polymers obtained by a polymerization process, wherein polymerization mixture comprises about 20 mol % of the monomer represented by formula VII.

In certain embodiments, the present invention relates to any of the aforementioned polymers obtained by a polymerization process, wherein polymerization mixture comprises between about 1 mol % and about 10 mol % of the crosslinker represented by formula VIII. In certain embodiments, the present invention relates to any of the aforementioned polymers obtained by a polymerization process, wherein polymerization mixture comprises between about 1 mol % and about 5 mol % of the crosslinker represented by formula VIII. In certain embodiments, the present invention relates to any of the aforementioned polymers obtained by a polymerization process, wherein polymerization mixture comprises about 3 mol % of the crosslinker represented by formula VIII.

In certain embodiments, the present invention relates to any of the aforementioned polymers obtained by a polymerization process, wherein polymerization mixture comprises between about 1 mol % and about 10 mol % of the initiator. In certain embodiments, the present invention relates to any of the aforementioned polymers obtained by a polymerization process, wherein polymerization mixture comprises between about 1 mol % and about 5 mol % of the initiator. In certain embodiments, the present invention relates to any of the aforementioned polymers obtained by a polymerization process, wherein polymerization mixture comprises about 2.5 mol % of the initiator.

Initiators

The initiator used in the present invention may be any suitable initiator.

In certain embodiments, the initiator is a radical initiator. Radical initiators are substances that can produce radical species under mild conditions and promote radical polymerization reactions. Initiators may be any commonly used initiator for polymerization such as, but not limited by, halogen molecules, azo compounds, and organic peroxides.

Like all diatomic molecules, halogens can generate two free radicals resulting from the homolysis of the bond, but halogens undergo the homolytic fission relatively easily. Chlorine, for example, gives two chlorine radicals (Cl.) by irradiation with ultraviolet light. This process is used for chlorination of alkanes.

Azo compounds (R'—N=N—R") can be the precursor of two carbon-centered radicals (R'. and R".) and nitrogen gas upon heating and/or by irradiation. For example, AIBN and ABCN yield isobutyronitrile and cyclohexanecarbonitrile radicals, respectively.

Organic peroxides each have a peroxide bond (—O—O—), which is readily cleaved to give two oxygen-centered radicals. The oxyl radicals are rather unstable and believed to be transformed into relatively stable carbon-centered radicals. For example, di-t(tertiary)-butylperoxide (tBuOOtBu) gives two t-butanoyl radicals (tBuO.) and the radicals become methyl radicals ($H_3C$.) with the loss of acetone. Benzoyl peroxide (($PhCOO)_2$) generates benzoyloxyl radicals (PhCOO.), each of which loses carbon dioxide to be converted into a phenyl radical (Ph.). Methyl ethyl ketone peroxide is also common, and acetone peroxide is on rare occasions used as a radical initiator, too.

In certain embodiments, initiators may be any commonly used initiator for cationic polymerization of vinyl ethers such as, but not limited by, triflic acid, $TiCl_4$, $BF_3.OEt_2$, $BF_3$, $BCl_3$, $SnCl_4$, $H_2SO_4$, $HI/I_2$, $AlCl_3$, $ZnBr_2$ or any other Lewis acid, with or without the co-reagents such as tertiary amines as is known to those skilled in the art of cationic and living cationic polymerizations.

In certain embodiments, the initiator is added portionwise while the polymerization progresses. In certain embodiments, the initiator is AIBN.

In certain embodiment, the initiator is tethered to a solid support, such as carbon black. When such a tethered initiator is used, the polymer formed it covelently bound to the solid support of the initiator. If a solid support has multiple initiators bound to it, this can result in a the preparation of a solid support which is bound to multiple polymers.

Crosslinkers

Crosslinkers are a series of connected atoms that link a first polymer backbone to a second polymer backbone via the atoms in a side chain on the first polymer backbone and the atoms in a side chain on a second polymer backbone. A crosslinked subunit, as used herein, refers to the atoms which make up part of the first polymer backbone and part of the second polymer backbone, as well as the atoms in the two side chains the crosslinker. The crosslinkers used in the present invention may be any suitable crosslinker.

The crosslinker(s) may, for example, be selected from 1,4-butanediol divinyl ether or any derivatives thereof containing alkyl, aryl, arylalkyl, alicylic, heteroaryl, heterocyclic, substituted alkyl, substituted aryl, substituted alicyclic, substituted heteroaryl, substituted heterocyclic or substituted arylalkyl groups or any other group that can easily be further functionalized by reactions commonly used in organic synthesis and where these groups are, optionally, conveniently protected for the purpose of the polymerization reaction.

The crosslinker(s) may, for example, be selected from ethylene glycol divinyl ether, 1,3-propanediol divinyl ether, 1,5-pentadiol divinyl ether, 1,6-hexanediol divinyl ether, 1,7-heptanediol divinyl ether, 1,8-octanediol divinyl ether, diethylene glycol divinyl ether, triethylene glycol divinyl ether, tetraethylene glycol divinyl ether or any derivatives thereof containing alkyl, aryl, arylalkyl, alicylic, heteroaryl, heterocyclic, substituted alkyl, substituted aryl, substituted alicyclic, substituted heteroaryl, substituted heterocyclic or substituted arylalkyl groups or any other group that can easily be further functionalised by reactions commonly used in organic synthesis and where these groups are, optionally, conveniently protected for the purpose of the polymerization reaction.

In certain embodiments, levels of crosslinking will vary between 0.5% and 10% of crosslinker, but other levels of crosslinking are also covered within the scope of this invention. In certain embodiments, the crosslinker is N,N'-methylenebisacrylamide (BIS) or ethylene glycol dimethacrylate (EGDMA).

Polymers Associated with Substrates and Redox Polymer Electrodes

Certain aspects of the invention relate a polymer, as described above, associated with a substrate. The phrase "associated with" means the condition in which two or more substances having any type of physical contact. For example, when a polymeric material is "associated with" a substrate, the polymeric material may be deposited or formed on the surface of the substrate, or, if the substrate is porous, within the pores of the substrate, through any type of physical or chemical interactions (such as through covalent bond, ionic bond, or van der Waal's bond), or through impregnating, intercalating, or absorbing.

In certain embodiments, the present invention relates to any of the aforementioned polymers associated with a substrate, wherein the substrate is a carbon particle, a carbon fiber or a metal wire mesh. In certain embodiments, the present invention relates to any of the aforementioned polymers associated with a substrate, wherein the metal wire mesh comprises gold, silver or platinum.

Another aspect of the invention relates to a redox polymer electrode comprising a particle associated with a conducting surface; wherein the particle is associated with one or more aforementioned polymer. In certain embodiments, the present invention relates to any of the aforementioned redox polymer electrodes, wherein the polymer is covalently bound to the particle.

In certain embodiments, the present invention relates to any of the aforementioned redox polymer electrodes, wherein the particle is carbon black. In certain embodiments, the present invention relates to any of the aforementioned redox polymer electrodes, wherein the conducting surface is carbon paper. In certain embodiments, the present invention relates to any of the aforementioned redox polymer electrodes, wherein the conducting surface is a wire mesh. In certain embodiments, the present invention relates to any of the aforementioned redox polymer electrodes, wherein the wire mesh comprises gold, silver or platinum.

In certain embodiments, the present invention relates to any of the aforementioned redox polymer electrodes, further comprising a binder. In certain embodiments, the present invention relates to any of the aforementioned redox polymer electrodes, wherein the binder is polytetrafluoroethylene (PTFE).

Methods of Isolating Organic Compounds from Aqueous Mixtures

As noted above, redox polymers as disclosed herein can be used to extract one compound from a solution, and then release the extracted compound based on a change in the polymer's redox state (i.e. charge). For example, the polymers described herein may be useful to separate alcohols from fermentation broths.

One aspect of the invention relates to a method isolating an organic compound from a first aqueous solution an releasing the organic compound into a second aqueous solution comprising the steps of:

contacting the first aqueous solution with a polymer of claim 1, thereby adsorbing the organic compound onto the polymer;

contacting the polymer with the adsorbed organic compound with a second aqueous solution; and oxidizing the redox-reactive moieties of the polymer with the adsorbed organic compound, thereby increasing the hydrophilicity of the polymer and de-adsorbing the adsorbed organic compound into the second aqueous solution.

Another aspect of the invention relates to a method of transferring an alcohol from a first aqueous solution to a second aqueous solution comprising the steps of:

contacting the first aqueous solution with a polymer of claim 1, thereby adsorbing the alcohol onto the polymer;

contacting the polymer with the adsorbed alcohol with a second aqueous solution; and oxidizing the redox-reactive moieties of the polymer with the adsorbed alcohol, thereby increasing the hydrophilicity of the polymer and de-adsorbing the adsorbed alcohol into the second aqueous solution.

In certain embodiments, the present invention relates to any of the aforementioned methods, wherein the first aqueous solution is a fermentation broth.

In certain embodiments, the present invention relates to any of the aforementioned methods, wherein the alcohol is butanol.

In certain embodiments, the present invention relates to any of the aforementioned methods, wherein the polymer is any of the aforementioned polymers.

Separations Systems

Another aspect of the invention relates to a separation system comprising any one or more of the aforementioned polymers, particles or redox polymer electrodes.

Another aspect of the invention relates to an in-situ continuous separation system comprising any one or more of the aforementioned polymers, particles or redox polymer electrodes.

In certain embodiments, the present invention relates to any of the aforementioned separation systems, wherein the separation system utilizes any of the aforementioned methods.

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The term "alkenyl" as used herein, means the radical formed by removing one hydrogen atom from a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyloxy" means an alkyl group, as defined herein, appended to the parent molecular moiety through an oxygen atom. Representative examples of alkyloxy include, but are not limited to, methoxy, ethoxy, propoxy, 2-propoxy, butoxy, tert-butoxy, pentyloxy, and hexyloxy.

The term "alkyloxycarbonyl" means an alkyloxy group, as defined herein, appended to the parent molecular moiety through a carbonyl group, represented by —C(=O)—, as defined herein. Representative examples of alkyloxycarbonyl include, but are not limited to, methoxycarbonyl, ethoxycarbonyl, and tert-butoxycarbonyl.

The term "alkyloxysulfonyl" as used herein, means an alkyloxy group, as defined herein, appended to the parent molecular moiety through a sulfonyl group, as defined herein. Representative examples of alkyloxysulfonyl include, but are not limited to, methoxysulfonyl, ethoxysulfonyl and propoxysulfonyl.

The term "arylalkyloxy" and "heteroalkyloxy" as used herein, means an aryl group or heteroaryl group, as defined herein, appended to the parent molecular moiety through an alkyloxy group, as defined herein. Representative examples of arylalkyloxy include, but are not limited to, 2-chlorophenylmethoxy, 3-trifluoromethylethoxy, and 2,3-methylmethoxy.

The term "arylalkyl" as used herein, means an aryl group, as defined herein, appended to the parent molecular moiety through an alkyl group, as defined herein. Representative examples of alkyloxyalkyl include, but are not limited to, tert-butoxymethyl, 2-ethoxyethyl, 2-methoxyethyl, and methoxymethyl.

The term "alkyl" means the radical formed by removing one hydrogen atom from a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylene" pertains to a bidentate (diradical) moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, —$(CH_2)_n$— where n is an integer from 1 to 10, for example, —$CH_2$—(methylene), —$CH_2CH_2$—(ethylene), —$CH_2CH_2CH_2$—(propylene), —$CH_2CH_2CH_2CH_2$—(butylene), —$CH_2CH_2CH_2CH_2CH_2$—(pentylene) and —$CH_2CH_2CH_2CH_2CH_2CH_2$—(hexylene). Examples of branched saturated $C_{1-10}$alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—. Examples of linear partially unsaturated $C_{1-10}$alkylene groups include, but are not limited to, —CH=CH—(vinylene), —CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—. Examples of branched partially unsaturated $C_{1-10}$alkylene groups include, but are not limited to, —C($CH_3$)=CH—, —C($CH_3$)=CH—$CH_2$—, and —CH=CH—CH($CH_3$)—. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene).

In general "-enes" refer to bidentate radicals (such as alkylene described above) and "-triyls" refer to tridentate radicals. For example, alktriyl refers to the radical formed by removing three hydrogen atoms from different carbons in a straight or branched chain hydrocarbon containing from 1 to 10 carbon atoms.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means the radical formed by removing one hydrogen atom from a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "amino" as used herein, refers to radicals of both unsubstituted and substituted amines appended to the parent molecular moiety through a nitrogen atom. The substituents are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicylic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the present invention can be optionally substituted with one, two, three, four, or five substituents independently selected from the group consisting of alkenyl, alkyloxy, alkyloxycarbonyl, alkyloxysulfonyl, alkyl, alkylcarbonyl, alkylcarbonyloxy, alkylsulfonyl, alkylthio, alkynyl, amido, amino, carboxy, cyano, formyl, halo, haloalkyloxy, haloalkyl, hydroxyl, hydroxyalkyl, mercapto, nitro, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-yl-ethyl.

The term "arylalkyloxy" or "arylalkyloxy" as used herein, means an arylalkyl group, as defined herein, appended to the parent molecular moiety through an oxygen. The term "heteroarylalkyloxy" as used herein, means an heteroarylalkyl group, as defined herein, appended to the parent molecular moiety through an oxygen.

The term "arylalkylthio" as used herein, means an arylalkyl group, as defined herein, appended to the parent molecular moiety through an sulfur. The term "heteroarylalkylthio" as used herein, means an heteroarylalkyl group, as defined herein, appended to the parent molecular moiety through an sulfur.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(=O)— group.

The term "carboxy" as used herein, means a —CO$_2$H group.

The term "cycloalkyl" as used herein, means the radical formed by removing one hydrogen atom from a monocyclic or a multicyclic (e.g., bicyclic, tricyclic, etc.) hydrocarbon containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkyloxy" as used herein, means a cycloalkyl group, as defined herein, appended to the parent molecular moiety through an oxygen.

The term "cyano" as used herein, means a —CN group.

The term "formyl" as used herein, means a —C(=O)H group.

The term "halo" or "halogen" means —Cl, —Br, —I or —F.

The term "haloalkyloxy" as used herein, means at least one halogen, as defined herein, appended to the parent molecular moiety through an alkyloxy group, as defined herein. Representative examples of haloalkyloxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl," as used herein, efers to the radical formed by removing a hydrogen atom from a non-aromatic ring system, including, but not limited to, monocyclic, bicyclic and tricyclic rings, which can be completely saturated or which can contain one or more units of unsaturation (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, or 3 substituents independently selected from alkenyl, alkyloxy, alkyloxycarbonyl, alkyloxysulfonyl, alkyl, alkylcarbonyl, alkylcarbonyloxy, alkylsulfonyl, alkylthio, alkynyl, amido, amino, carboxy, cyano, formyl, halo, haloalkyloxy, haloalkyl, hydroxyl, hydroxyalkyl, mercapto, nitro, silyl and silyloxy. Radicals wherein 1, 2, or 3 of the carbon atoms in the heterocyclyl ring (e.g. —CH$_2$— and —C(H)=), as defined above, can be replaced with —C(=O)— and the resulting radical is also heterocyclyl.

The term "heteroaryl" as used herein, efers to the radical formed by removing hydrogen from an aromatic ring systems, such as, but not limited to, monocyclic, bicyclic and tricyclic rings, that have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, or 3 substituents independently selected from alkenyl, alkyloxy, alkyloxycarbonyl, alkyloxysulfonyl, alkyl, alkylcarbonyl, alkylcarbonyloxy, alkylsulfonyl, alkylthio, alkynyl, amido, amino, carboxy, cyano, formyl, halo, haloalkyloxy, haloalkyl, hydroxyl, hydroxyalkyl, mercapto, nitro, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, which is appended to the parent molecule through an oxygen atom.

The term "silylenes" refers to chemical compounds containing a divalent and dicoordinate silicon atom without any electrical charge.

The term "redox-responsive moiety" refers to any chemical moiety capable of undergoing a reduction (accepting of an electron or electrons) or oxidation (donation of an electron or electrons). For example, the term redox-responsive moiety includes organic redox couples (e.g., viologens, quinines, and hydroquinines), organometallic materials (e.g., metallocenes), and inorganic materials (e.g., Ruthenium examine or Indium hexachloride). In certain embodiments the redox-responsive moiety can comprise, for example, a metal or a metal ion of any suitable element, such as Cu, Ag, Au, Sn, Fe, Ni, Ru, Ti, Ta, Nb, Hf, W, Y, Zn, Zr, Al, La, Ce, Pr, Nd, Sm, Sb, Bi, Pb, Tl, In, Te, Cr, V, Mn, Mo, Co, Rh, Pd, Pt, Cd, Os, Re, Ir, Hg, and mixtures thereof. In addition, the redox-responsive moiety can also be an oxide, a salt, or an organo- or inorganic complex, of any suitable element.

The term "hydrophilic" refers to any chemical species or subgroup with a high affinity for aqueous solutions, such as water. Therefore, a hydrophilic compound tends to be attracted to, dissolve in, or be absorbed in an aqueous solution.

The term "hydrophobic" refers to any chemical species or subgroup with a low affinity for aqueous solutions, including water. Therefore, a hydrophobic compound tends to repel and not be absorbed in an aqueous solution.

The term "monomer equivalent" refers to a monomer which would have led to the polymer even though the polymer was formed by a post-polymerization reaction rather than directly formed by the polymerization of that monomer.

The term "metallocene" refers to a transition metal and two cyclopentadienyl ligands coordinated in a sandwich structure, i.e., the two cyclopentadienyl anions are co-planar with equal bond lengths and strengths. An example of a metallocene is bis($\eta^5$-cyclopentadienyl)-iron(II), which is known as ferrocene. Metallocenes can be oxidized to form metallocenium cations.

The term "sequential addition" as used herein indicates that a percentage of a component is added to a mixture, a period of time is allowed to pass, another percentage of the component is added to a mixture, another period of time is allowed to pass, and the process is continued until all of the component has been added to the mixture.

The term "mol %" as used herein, refers to the mole percentage of one component in a mixture relative to all the other components in the mixture. For example, for a mixture that contains a first monomer, a second monomer, a crosslinker and an initiator, the mol % of the first monomer can be found by dividing the number of moles of the first monomer by the sum of the number of moles of the first monomer, second monomer, crosslinker and initiator.

As used herein, the term "polymer" means a molecule, formed by the chemical union of two or more subunits. The chemical subunits are normally linked together by covalent linkages. The two or more combining subunits in a polymer can be all the same, in which case the polymer is referred to as a homopolymer. They can be also be different and, thus, the polymer will be a combination of the different subunits; such polymers are referred to as copolymers.

As used herein, the "main chain" of a polymer, or the "backbone" of the polymer, is the series of bonded atoms that together create the continuous chain of the molecule. As used herein, a "side chain" of a polymer is the series of bonded atoms which are pendent from the main chain of a polymer.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

"Terathane® Polytetramethylene ether glycol" or PTMEG (also referred to as PTMO or, PTMG) is a family of linear diols in which the hydroxyl groups are separated by repeating tetramethylene ether groups. For example, in Terathane® 1000 n averages 14 or in Terathane® 2000, n averages about 27.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation and Properties of HBMA-VF Gels

Polymer gels synthesized using hydroxybutyl methacrylate (HBMA) and vinylferrocene (VF) as co-monomers, cross-linked using N,N'-methylenebisacrylamide (BIS) or ethylene glycol dimethacrylate (EGDMA), and initiated using 2,2'-azobis(isobutyronitrile) (AIBN) as the free radical initiator, showed preferential selectivity for low molecular weight alcohols, like ethanol and butanol, over water. In addition, the presence of ferrocene groups in the gel made it possible to increase the hydrophilicity of the gel matrix, and reduce its affinity for alcohol, by using a suitable oxidizing agent to convert the ferrocene groups to ferrocenium ions.

For the application of the polymer gels to commercial separation systems aimed at separating butanol from its aqueous solution, the difference in the selectivity of the gels for BuOH in the reduced and the oxidized states should be relatively large. In order to arrive at the synthesis recipe which would result in gels that could selectively extract BuOH in the reduced state and could release a large fraction of the absorbed BuOH on oxidation of the ferrocene moieties, a series of polymer gels of different compositions, described in FIG. 1, were synthesized by bulk free radical polymerization and their solvent uptake behavior was examined in both the reduced state and on oxidation using $FeCl_3$.

Figure 3:
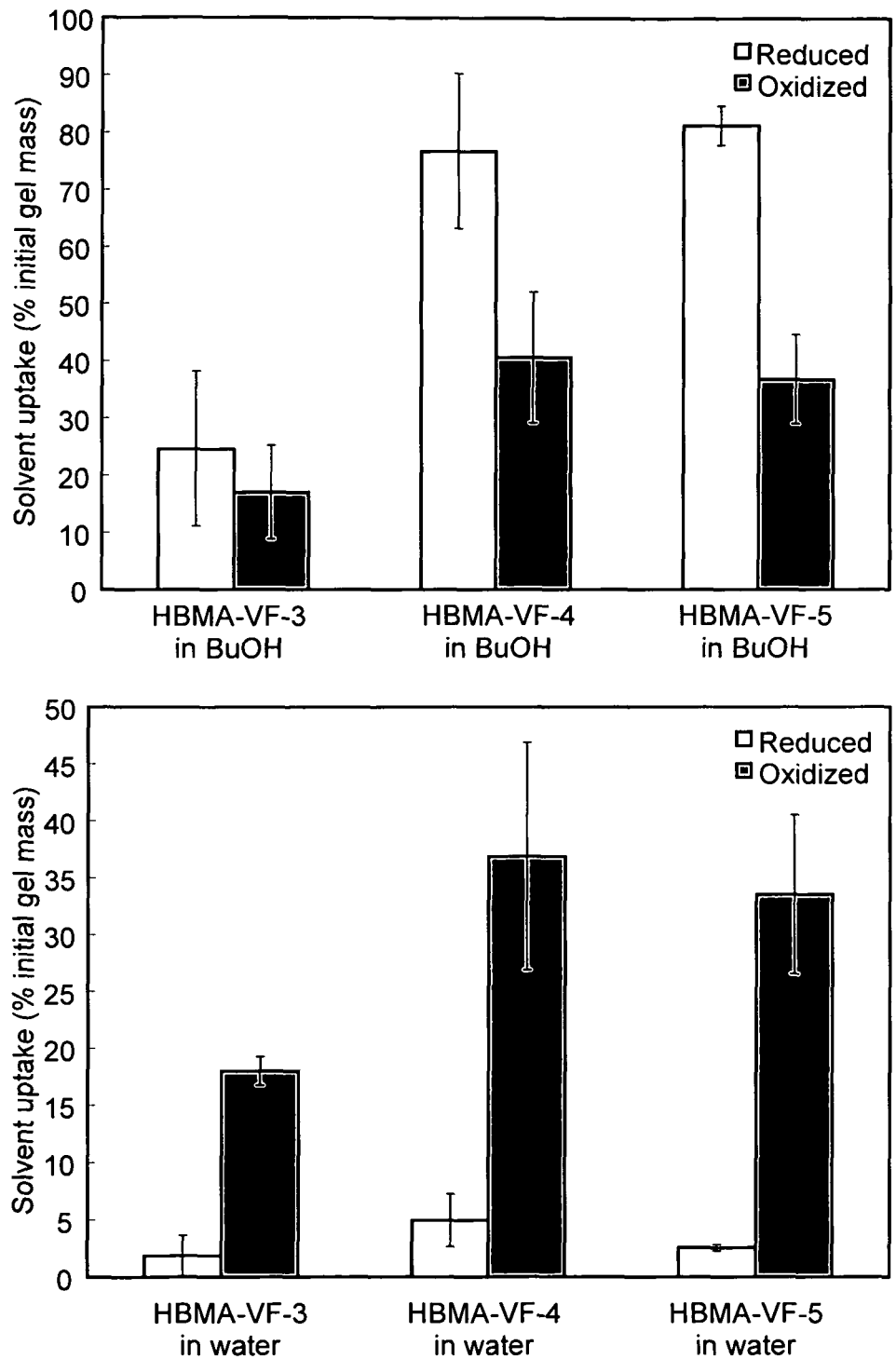
FIG. 3 depicts bar graphs showing uptake of solvent by HBMA-VF-3, HBMA-VF-4, HBMA-VF-5 gels (gels with high VF content) in the reduced and the oxidized states when immersed in BuOH (top bar graph) or water (bottom bar graph).

It was found that the gels with low VF content, HBMA-VF-1 and HBMA-VF-2, did not show considerable decrease in the preference for BuOH on oxidation (FIG. 2). Attempts to synthesize solid polymer gels with high ferrocene content (>5 mol %) met with failure when the polymerization was carried out in solution. Bulk polymerization proved to be successful, although the limited solubility of VF in HBMA did not allow the VF content of the gels to be increased beyond a critical value. The gels HBMA-VF-3, HBMA-VF-4, and HBMA-VF-5 with high VF content of nearly 20 mol % showed significant decrease in the preference for BuOH and increase in the preference for water upon oxidation (see FIG. 3).

The synthesized gels were found to demonstrate increase in solvent uptake upon decrease in molar percentage of the cross-linker added which can be explained to be a result of the high mechanical rigidity of the gels with high cross-linker content which prevented the stretching of the gel matrix to incorporate more solvent. It was also found that if the gels were synthesized, as suggested by Sasaki et al. [Y Sasaki; L L Walker; E L Hurst; C U Pittman Jr., *J. Polym. Sci.*, 1973, 11, 1213-1224], by the sequential addition of the initiator, the resulting gel, HBMA-VF-5, showed a higher percentage increase in the affinity for water in the oxidized state than in the reduced state. Therefore, the composition and the recipe for the preparation of HBMA-VF-5 was chosen as the most optimum for the desired use in the design of the continuous separation system for separating butanol from its aqueous fermentation broth.

Example 2

Measurement of Equilibrium Distribution Coefficient and Separation Factor for Butanol Extraction by HBMA-VF-5 Gel Pieces of HBMA-VF-5 gel were weighed and immersed in 1 mL BuOH-water solution with the BuOH content ranging from 1 to 8% by volume, and allowed to swell to equilibrium over a period of 48 hours. The volume of the supernatant BuOH-water solution was measured to determine the solvent uptake by the gel. The swollen gel was weighed to check the accuracy of the measurement. The concentration of BuOH in the supernatant was determined using Gas Chromatography (GC). The concentration of water in the supernatant was obtained by difference. By conserving the total moles of BuOH and water, the concentrations of the species in the gel phase were obtained. The calculated values of the concentrations of BuOH and water in the gel and the aqueous phase (denoted by c) were used to calculate the equilibrium distribution coefficient ($K_D$) of BuOH and water and separation factor ($\alpha$) for BuOH extraction in the reduced state according to equation (1).

Figure 4A:
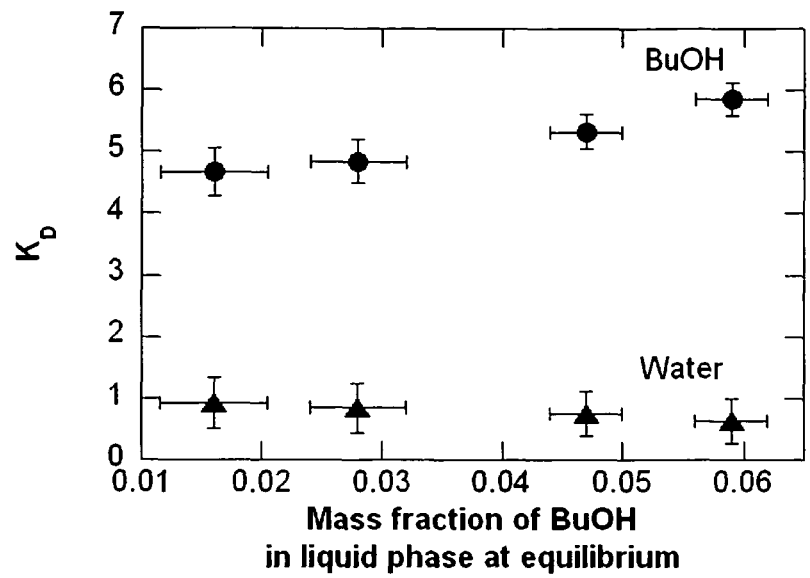
FIGS. 4A-C depict graphs showing variation of $K_D$ and $\alpha$ with initial BuOH content of the supernatant for HBMA-VF-5 gel in the reduced (A) and oxidized states (B).
Figure 4B:
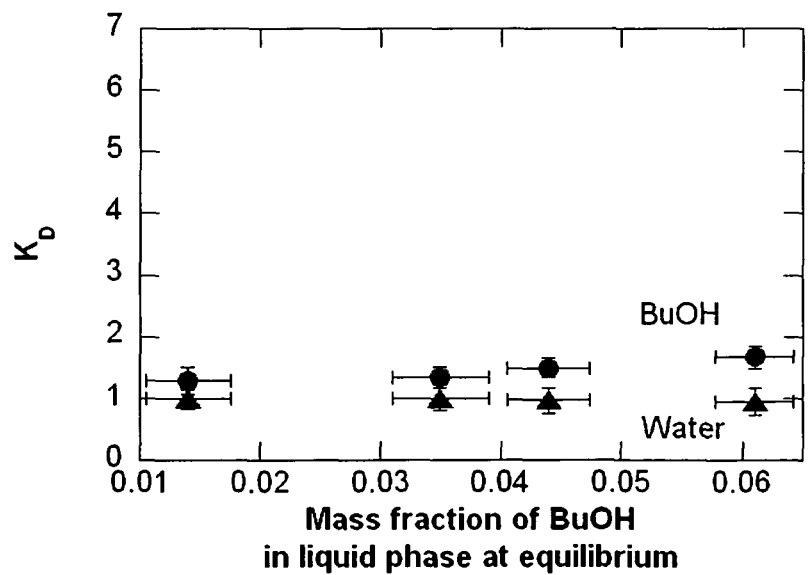
Figure 4C:
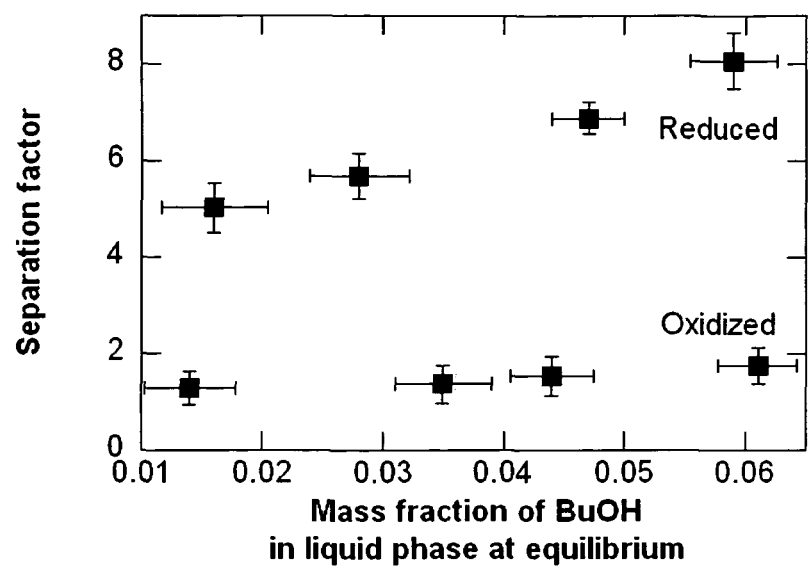

Experiment analogous to the one described above were carried out to measure $K_D$ and $\alpha$ for BuOH extraction by the gel in the oxidized state by allowing HBMA-VF-5 gel pieces to swell to equilibrium in a BuOH-water solution containing $FeCl_3$. The results obtained are plotted in FIG. 4 as a function of the initial BuOH content. The trends obtained for the variation in $K_D$ and $\alpha$ of the gel in the reduced state with the initial BuOH content are in agreement with similar measurements made in literature for solvents used in the liquid extraction of alcohols [R D Offeman; S K Stephenson; G H Robertson; W J Orts, *Ind. Eng. Chem. Res.*, 2005, 44, 6789-6796].

Example 3

Preparation of a HBMA-VF Redox Polymer Electrode (RPE)

Conductive carbon black (CB) particles were suitably surface modified using the procedure outlined by Tamaki and Yamaguchi [T Tamaki; T Yamaguchi, *Ind. Eng. Chem. Res.*, 2006, 45, 3050-3058] and Fujiki et al. [K Fujiki; N Tsubokawa; Y Sone, *Polym. J.*, 1990, 22, 661-670] to covalently attach free radical initiators to their surfaces.

Figure 5:
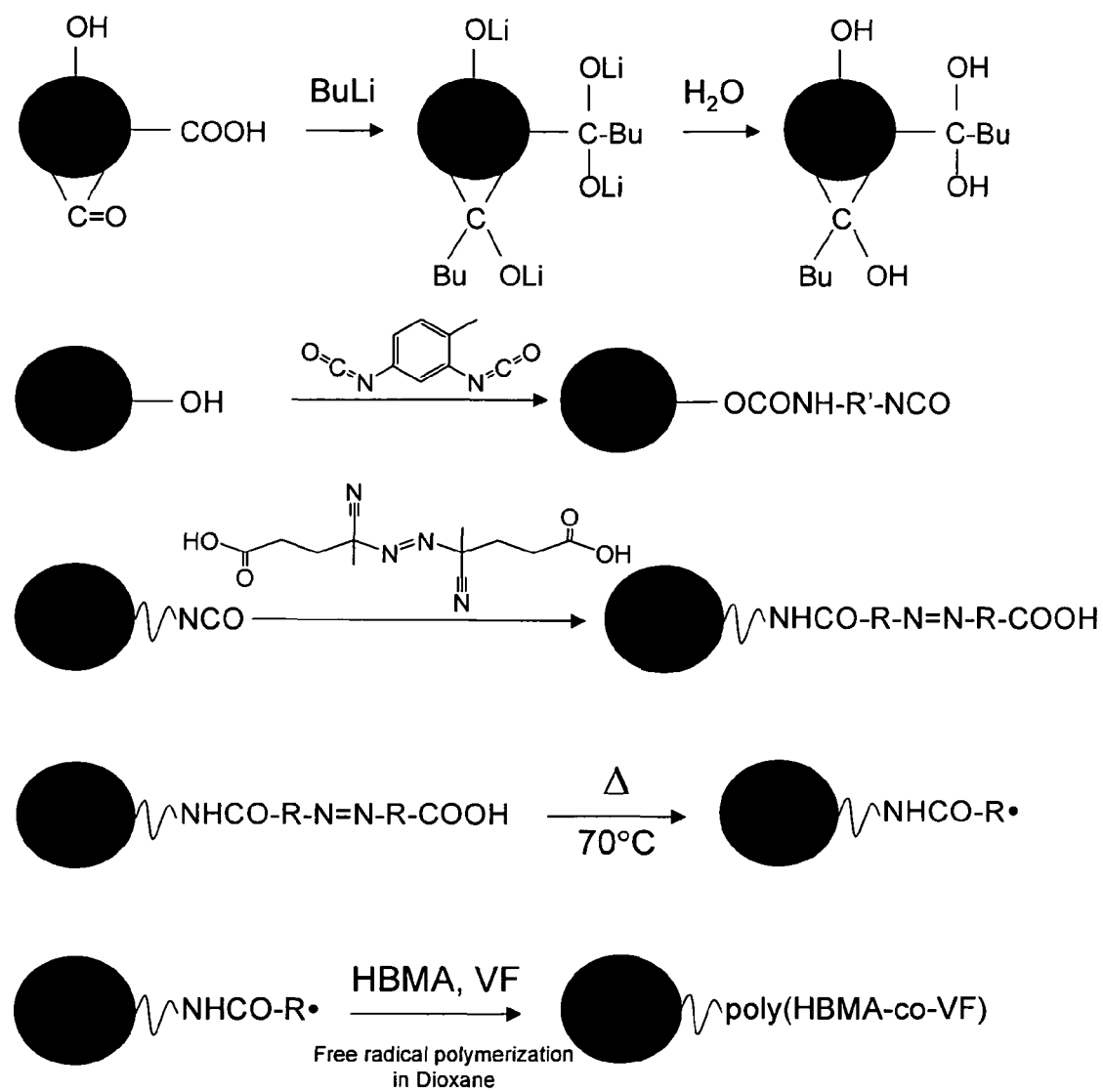
FIG. 5 depicts reaction steps involved in the attachment of HBMA, VF co-polymer on a carbon black (CB) surface by (a) introduction of hydroxyl groups on CB surface, (b) attachment of diisocyanate to the CB surface, (c) introduction of azo-bis group, (d) generation of free radical by decomposition of azo-bis compound, and (e) growth of polymer chain on CB.

The functional groups on the surface of carbon black were converted to —OH groups by reaction of CB with n-butyl lithium [K Fujiki; N Tsubokawa; Y Sone, *Polym. J.*, 1990, 22, 661-670]. These —OH groups were then made to react with a diisocyanate followed by reaction with 4,4'(azobis)cyanopentanoic acid. At the end of this step, the CB particles had a thermal free radical initiator covalently attached to their surface [T Tamaki; T Yamaguchi, *Ind. Eng. Chem. Res.*, 2006, 45, 3050-3058]. The modified CB particles were heated at 70° C. in a solution of HBMA and VF (the molar ratio of HBMA and VF having been kept the same as in HBMA-VF-5 gel) in dioxane for 24 hours to grow chains of copolymer of HBMA and VF attached to the CB surface. The chemical reactions involved in the surface modification of CB and subsequent growth of polymer chains attached to it are depicted in FIG. 5.

CB grafted with the redox polymer was filtered, washed with methanol and dried in vacuum, and the CB so obtained was mixed with polytetrafluoroethylene (PTFE) in the weight ratio 3:1 and isopropyl alcohol (IPA). PTFE was used as a binder for CB [L Bonnefoi; P Simon; J F Fauvarque; C Sarrazin; J F Sarrau; A Dugast, *J. Power Sources*, 1999, 80, 149-155; and L Fransson; T Eriksson; K Edstrom; T Gustafsson; J O Thomas, *J. Power Sources*, 2001, 101, 1-9]. The mixture of CB, PTFE and IPA was coated onto porous conducting carbon substrate, Toray carbon paper. The coated carbon paper was allowed to dry, and subsequently hot pressed at 130° C. by applying a pressure of 0.25 MPa to form a RPE.

Example 4

Characterization of a HBMA-VF Redox Polymer Electrode (RPE)

Electrochemical Characterization.

Figure 6:
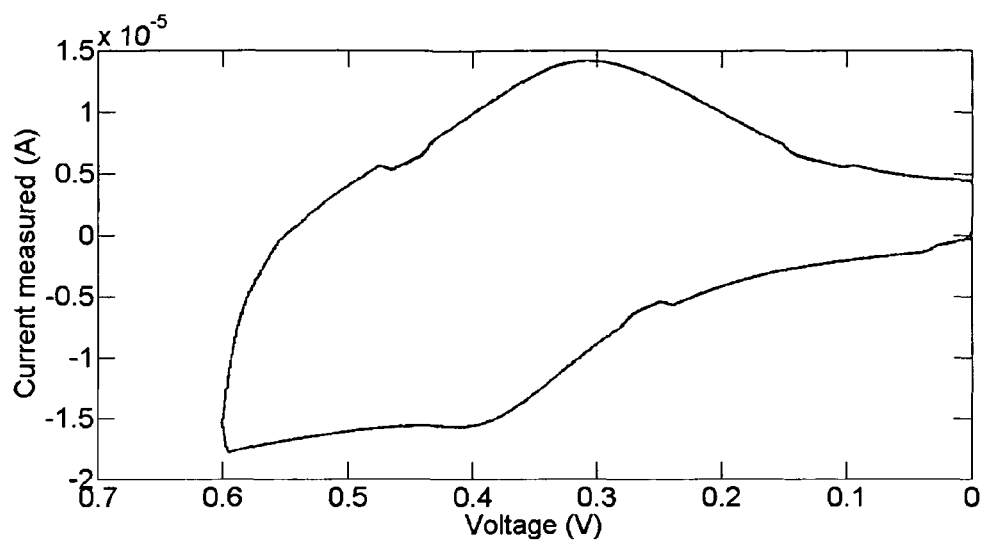
FIG. 6 depicts a voltammogram of a redox polymer electrode containing poly(HBMA-co-VF) obtained with reference to a SCE in 0.1M $NaNO_3$ solution in water.

The electrochemical activity of the RPE prepared was analyzed using cyclic voltammetry (CV). Saturated calomel electrode (SCE) was used as the reference electrode, and platinum foil formed the counter electrode. 0.1M $NaNO3$ solution in water was used as the electrolyte. The voltammogram obtained at a scan rate of 20 mV/s is shown in FIG. 6.

Figure 7:
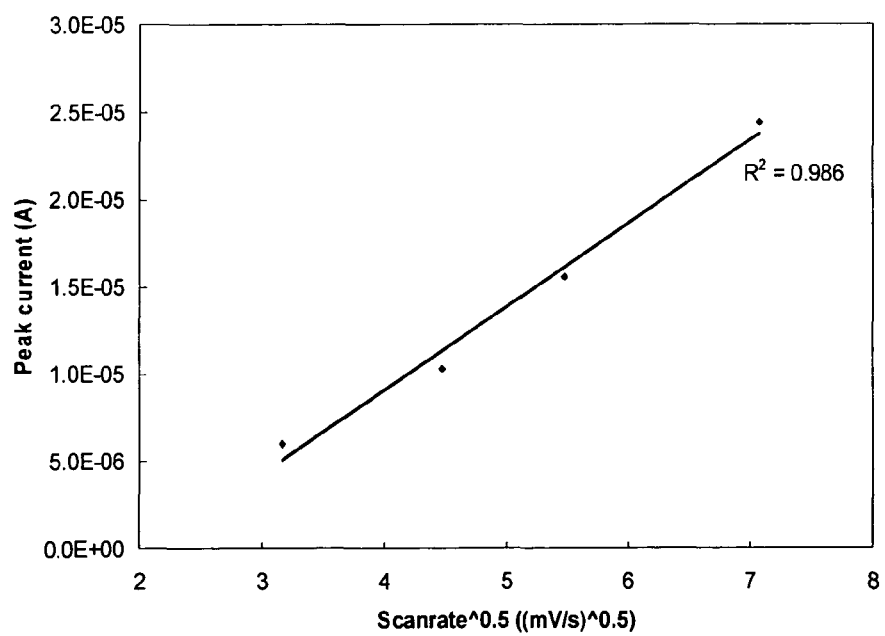
FIG. 7 depicts a graph showing variation of anodic peak current with square root of scan rate.

The voltammogram showed a one electron reversible oxidation and reduction at a mean potential of 0.355V vs. SCE, which is similar to the redox potential observed for ferrocene containing polymers in literature [S Nakahama; R W Murray, *J. Electroanal. Chem.*, 1983, 158, 303-322]. The reversibility of the redox reaction taking place was established by carrying out multiple potential sweep cycles, each of which resulted in almost similar voltammograms. The observed values of the peak currents varied linearly with the square root of the scan rate (FIG. 7), indicating that the transport of electrons by diffusion from the bulk electrolyte to the redox sites was the rate controlling step in the redox process.

Figure 8:
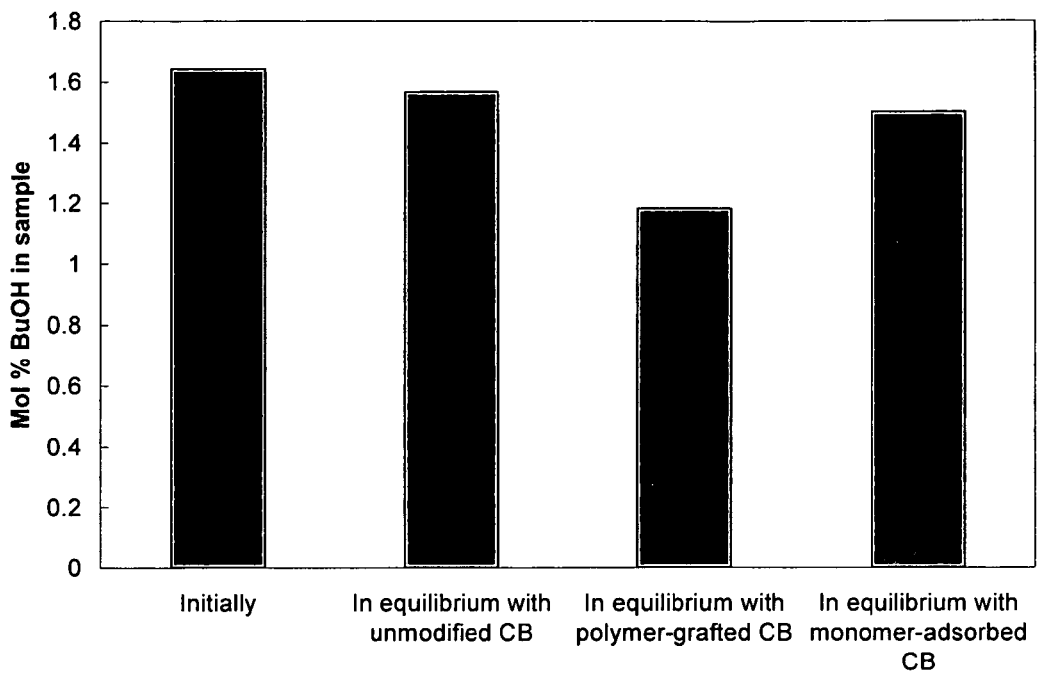
FIG. 8 depicts a bar graph comparing extraction of BuOH by unmodified, polymer grafted and monomer-adsorbed CB.
Figure 9:
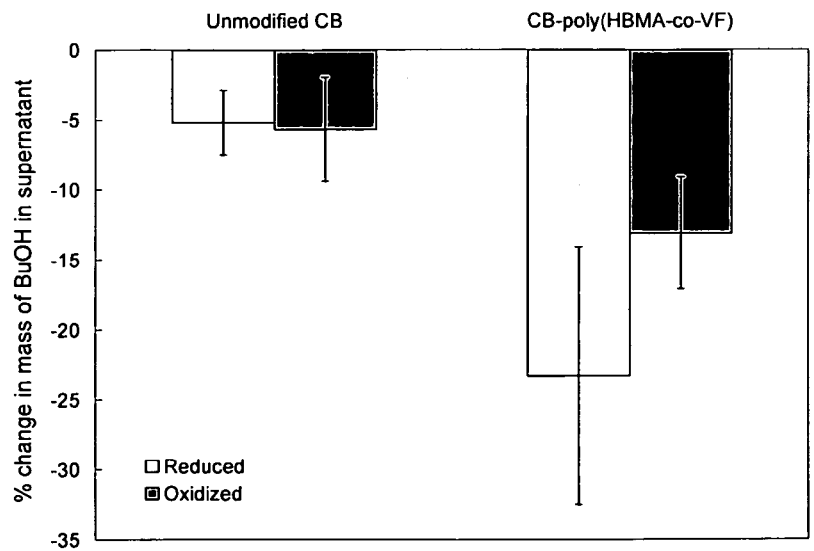
FIG. 9 depicts a bar graph showing the results of BuOH extraction by CB-poly(HBMA-co-VF). The CB grafted with polymer shows a decreased preference for butanol when oxidized.
Figure 10:
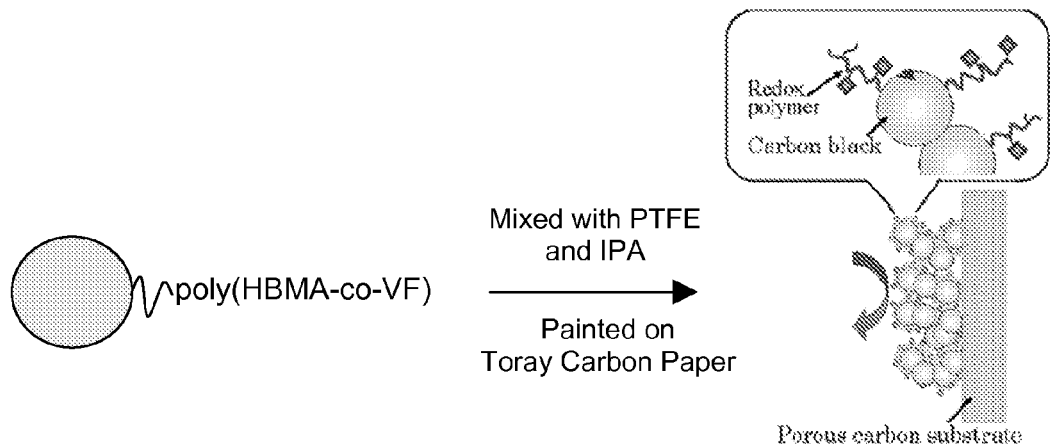
FIG. 10 depicts the preparation of a redox polymer electrode using CB grafted with poly(HBMA-co-VF) [T Tamaki; T Yamaguchi, *Ind. Eng. Chem. Res.,* 2006, 45, 3050-3058].
Figure 11:
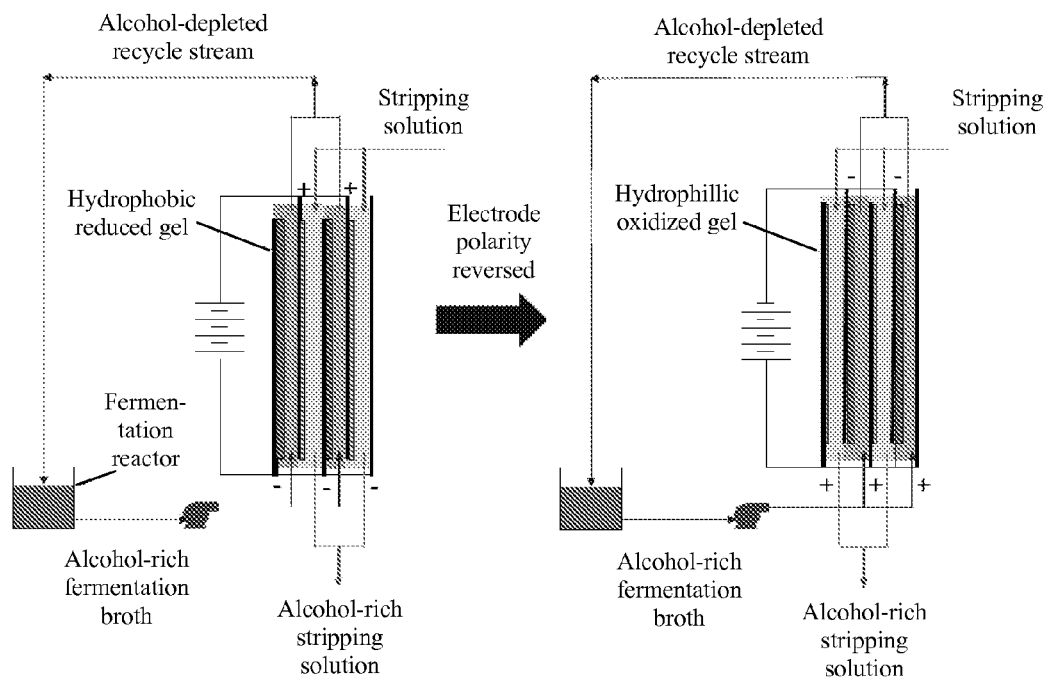
FIG. 11 depicts a schematic of one example of a continuous separation system which can be set-up by to continuously separate alcohol from the fermentation broth and release it into a stripping stream. When the polymer coated electrode is connected to the negative terminal of the potential source, the polymer is in reduced state and can extract alcohol from the fermentation broth flowing next to it. When it is saturated with the alcohol, the polarity of the potential source can be reversed and the extracted alcohol can be released into a stripping solution.
Figure 12:
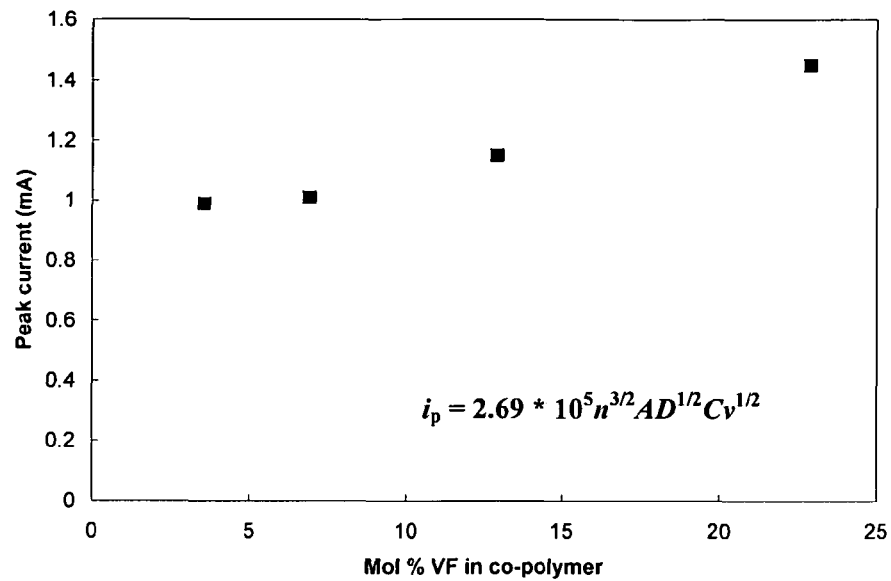
FIG. 12 depicts a plot showing peak current in CV as a function of mol % VF.

Measurement of Extraction of BuOH. The amount of BuOH that could be extracted using polymer-grafted CB was measured by adding 1 mL of 8% v/v (1.64 mol %) BuOH solution in water to a vial containing 0.1 g of the polymer grafted CB and allowing the system to equilibrate for 48 hours after which the contents of the vial were centrifuged to separate the CB and the BuOH content in the supernatant measured using GC. As a control, an analogous experiment was carried out in another vial containing 0.1 g of unmodified CB instead of the polymer-grafted CB. As another control, to ascertain if what we claimed to be polymer-grafted CB did indeed have polymer chains covalently attached to the CB surface and the electrochemistry and extraction we had measured were not due to surface adsorption effects, a fresh batch of modified CB was synthesized which did not have azo group attached to its surface, and therefore could not initiate the attachment of the polymeric chains to the CB surface. The CB from this batch was contacted with HBMA and VF in dioxane at the same conditions used for the polymer grafting, filtered, and dried. The extraction of BuOH by the CB thus obtained was also measured. The results are plotted in FIG. 8. The polymer grafted CB extracted 28% of the initial BuOH. The BuOH extraction by the unmodified CB and CB with adsorbed monomers was considerably lower.

Example 5

Figure 14:
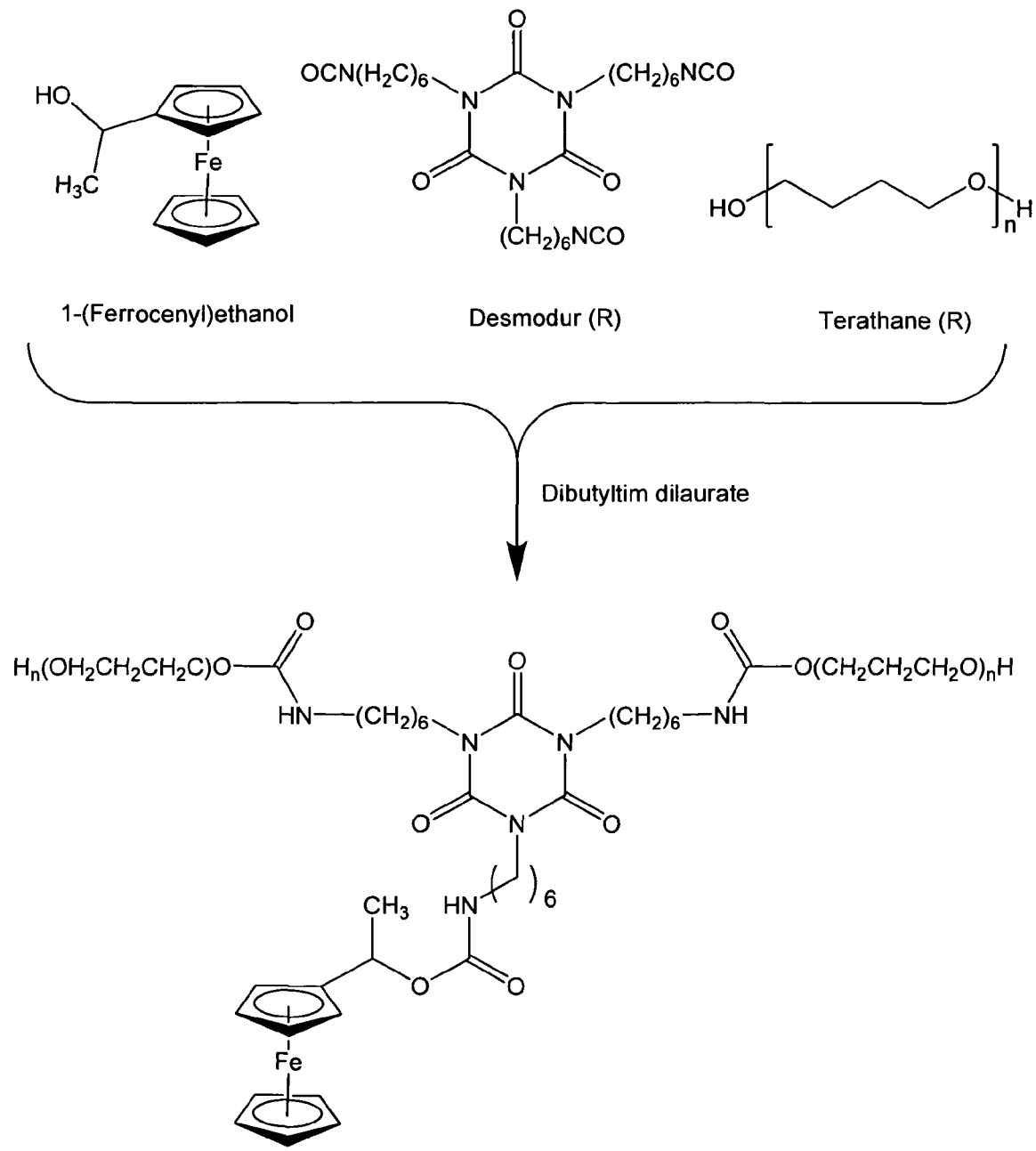
FIG. 14 depicts the schematic showing one route to the preparation of a polymer from Tetraethanes®, Desmodur® and 1-(ferrocenyl)ethanol in the presence of dibutyltin dilaurate.

Synthesis of a Redox Gel Made Up Of Polyether Backbone and Crosslinked by Formation of Polyurethane Bonds for Extraction of Butanol from Water Commercially available polyether, Terathane®, of different molecular weights was crosslinked using another commercially available trifunctional cross-linker, Desmodur®, in the presence of ferrocene containing compounds like 1-(ferrocenyl)ethanol. Solid redox gels resulted in each case. The chemical reaction leading to the formation of the gel is shown in the FIG. 14.

Figure 15:
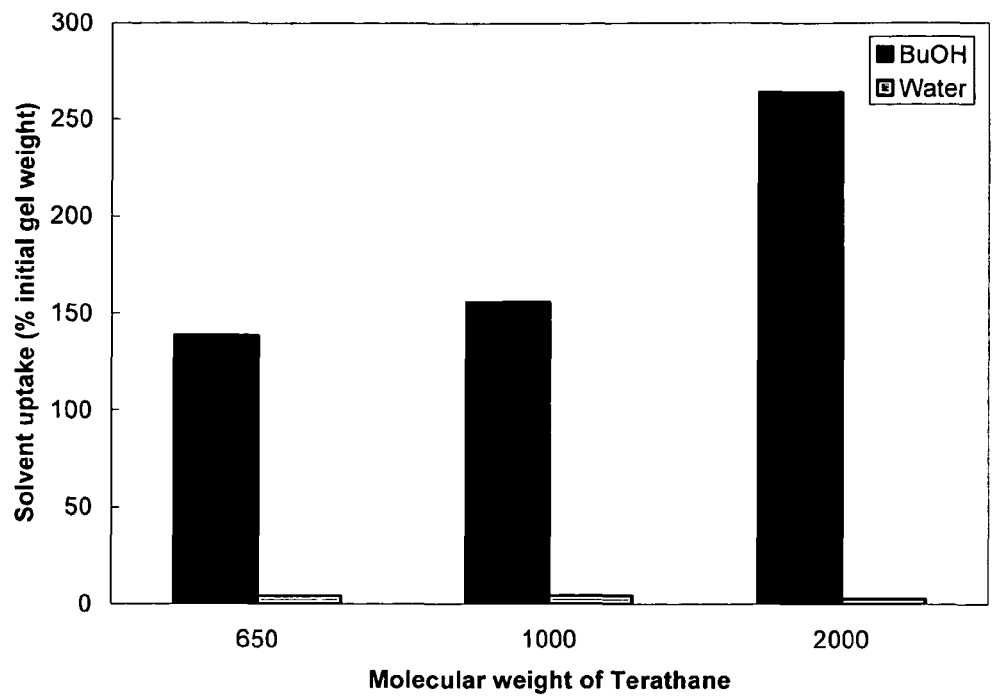
FIG. 15 depicts a graph showing the preference for gels made up of Terathane® of different molecular weights (650, 1000, and 2000) for butanol and water.

The gel thus prepared was shown to have high selectivity for butanol. FIG. 15 shows the preference for gels made up of Terathane® of different molecular weights for butanol and water. The gels are expected to show a decreased preference for butanol and an increased preference for water when the ferrocene groups in the gels are oxidized.

Example 6

RPE Prepared by Chemical Attachment of Redox Polymer on the Surface of Carbon Paper (CP)

Figure 13:
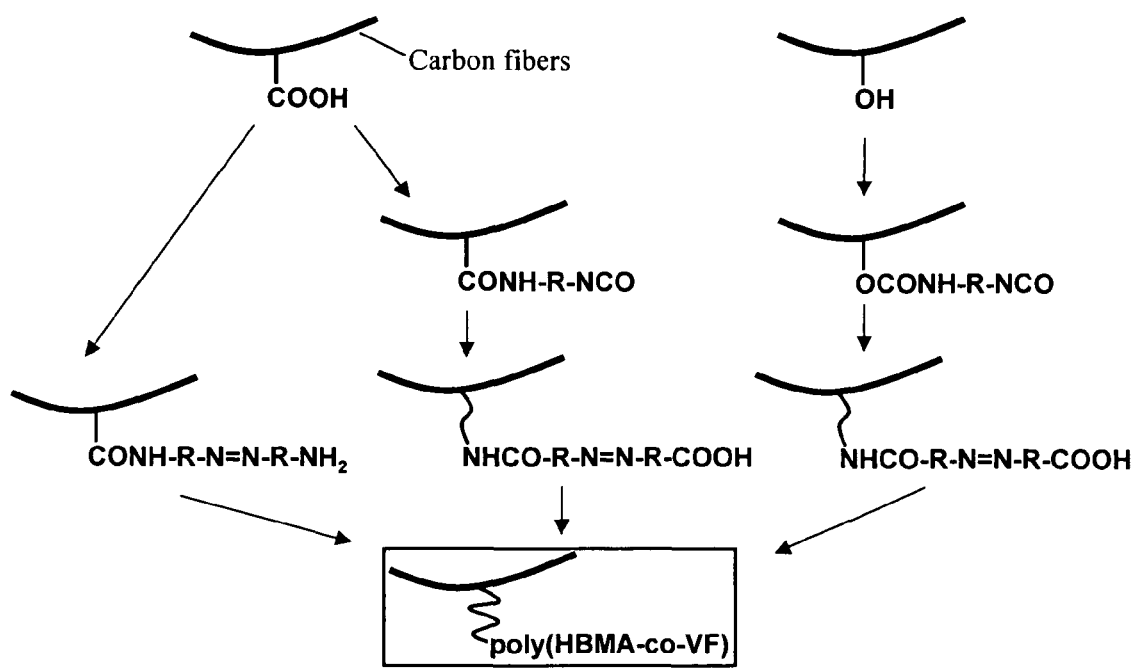
FIG. 13 depicts examples of approaches for grafting polymer chains onto carbon paper.

Carbon Paper (CP) is a mat of carbon fibers with high conductivity. The chemistry to modify carbon fiber to enable graft polymerization of vinyl monomers, namely methyl methacrylate, has been shown in literature [K Fujiki; N Motoji; A Yoshida, *Compos. Interfaces*, 1996, 3, 371-380]. Similar method to attach the redox polymer, a copolymer of HBMA and VF, to the carbon fibers. The experimental scheme is shown in FIG. 13.

Example 7

RPE Prepared by Embedding Conducting Fibers or Wires in a Redox Gel Matrix

Figure 16:
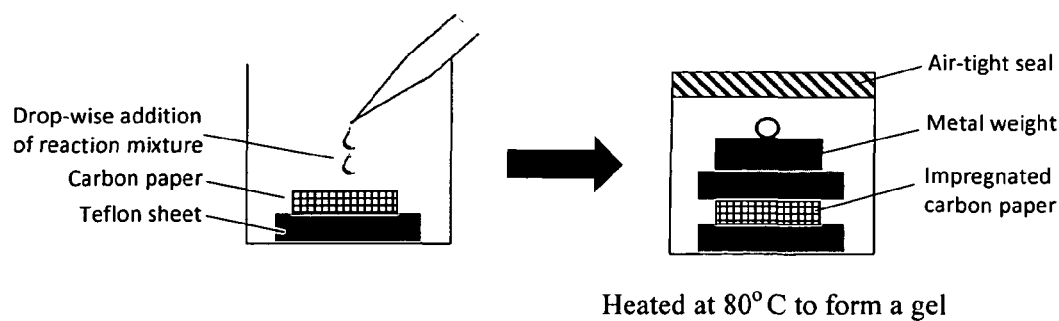
FIG. 16 depicts a schematic to illustrate the impregnation of conducting substrate by a redox gel.

Instead of attaching the redox polymer chemically to a conducting substrate like CB or CP, gelation was carried out around a porous conducting wire mesh. The material making up the wire mesh can be carbon fiber or any other metal wire. A solution of monomers (HBMA and VF) containing a crossinker (EGDMA) and initiator (AIBN) was added drop-wise to carbon paper in an inert atmosphere, and allowed to spread uniformly throughout the fiber mesh to wet the fibers. The composition of the monomer solution was the same as that used in the synthesis of HBMA-VF-5 gel. The carbon paper containing the monomer solution was, next, heated to allow the formation of gel around the carbon fiber matrix. The reaction scheme is illustrated below in FIG. 16. The electrode thus prepared was analyzed using cyclic voltammetry to prove its electrochemical activity.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by this disclosure.

We claim:

1. A polymer comprising a plurality of first subunits, a plurality of second subunits, and a plurality of third subunits wherein the first subunits are represented by formula I:

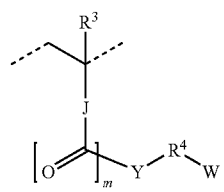

I the second subunits are represented by formula II:

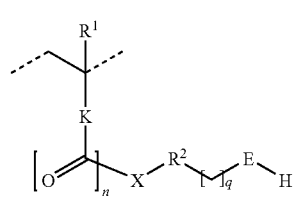

II and the third subunits are represented by formula VIII:

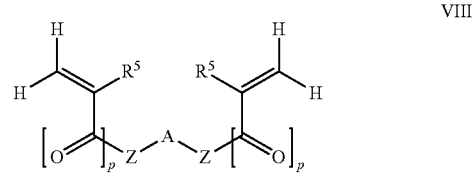

VIII wherein, independently for each occurrence,
A is alkylene;
E is —O—;
J is absent;
K is absent;
m is 0;
n is 1;
p is 1;
q is 0;
R is alkyl;
$R^1$ is hydrogen or alkyl;
$R^2$ is absent, alkylene, cycloalkylene, heterocyclylene, arylene, heteroarylene, cycloalkylalkylene, heterocyclylalkylene, arylalkylene or heteroarylalkylene;
$R^3$ is hydrogen;
$R^4$ is absent;
$R^5$ is alkyl;
W is a redox-responsive moiety;
X is —O—;
Y is absent;
Z is —O—; and
- - - - - - depicts a bond to a first subunit, a bond to a second subunit, a bond to a third subunit, a bond to a hydrogen atom, or a bond to a radical formed by the decomposition of an initiator, provided at least one - - - - - - depicts a bond to a radical formed by the decomposition of an initiator; and the polymer preferentially binds to an alcohol over water when the redox-responsive moieties are uncharged; and the polymer preferentially binds to water over the alcohol when the redox-responsive moieties are charged.

2. The polymer of claim 1, wherein the alcohol is butanol.

3. The polymer of claim 1, wherein the radical formed by the decomposition of the initiator is halo, alkyl, cyanoalkyl, cycloalkyl, aryl, heteroaryl, aralkyl, heteroaralkyl, alkyloxy, cycloalkyloxy, aryloxy, heteroaryloxy, aralkyloxy, heteroaralkyloxy, alkylcarbonyoxy, cycloalkylcarbonyoxy, arylcarbonyoxy, heteroarylcarbonyoxy, aralkylcarbonyoxy, or heteroaralkylcarbonyoxy.

4. The polymer of claim 1, wherein the radical formed by the decomposition of the initiator is tethered to a solid support.

5. The polymer of claim 4, wherein the solid support is carbon particles or carbon fibers.

6. The polymer of claim 1, wherein the polymer is associated with a substrate.

7. The polymer of claim 6, wherein the substrate is carbon particles, carbon fibers or a metal wire mesh.

8. A redox polymer electrode comprising the polymer of claim 6.

9. The polymer of claim 1, wherein, independently for each occurrence, W is ferrocenyl.

10. The polymer of claim 9, wherein, independently for each occurrence, $R^1$ is methyl; and $R^2$ is butylene.

11. The polymer of claim 10, wherein, independently for each occurrence, $R^5$ is methyl; and A is ethylene.

* * * * *